(12) United States Patent
Draborg et al.

(10) Patent No.: US 7,888,093 B2
(45) Date of Patent: Feb. 15, 2011

(54) SUBTILASE VARIANTS

(75) Inventors: Henriette Draborg, Allerod (DK); Peter Kamp Hansen, Lejre (DK); Mads Eskelund Bjornvad, Frederiksberg (DK); Mads Norregaard-Madsen, Birkerod (DK); Mikael Mikkelsen, Smorum (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 10/699,394

(22) Filed: Oct. 31, 2003

(65) Prior Publication Data

US 2004/0147008 A1    Jul. 29, 2004

Related U.S. Application Data

(60) Provisional application No. 60/507,537, filed on Oct. 1, 2003, provisional application No. 60/434,723, filed on Dec. 19, 2002, provisional application No. 60/427,156, filed on Nov. 18, 2002.

(30) Foreign Application Priority Data

Nov. 6, 2002  (DK) ............... 2002 01705
Dec. 18, 2002 (DK) ............... 2002 01933

(51) Int. Cl.
*C12N 9/54* (2006.01)
*C12N 9/56* (2006.01)
*C12N 15/57* (2006.01)
*C12N 15/74* (2006.01)
*C12N 15/75* (2006.01)
*C11D 3/386* (2006.01)

(52) U.S. Cl. ............... 435/221; 435/69.1; 435/222; 435/252.3; 435/252.35; 435/320.1; 536/23.2; 510/300

(58) Field of Classification Search ............... None
See application file for complete search history.

(56) References Cited

U.S. PATENT DOCUMENTS

| | | | | |
|---|---|---|---|---|
| 5,336,611 A * | 8/1994 | van Eekelen et al. | ......... | 435/221 |
| 5,340,735 A * | 8/1994 | Christianson et al. | ....... | 435/221 |
| 5,389,307 A | 2/1995 | Lindegaard et al. | | |
| 5,482,849 A * | 1/1996 | Branner et al. | ............... | 435/222 |
| 5,500,364 A * | 3/1996 | Christianson et al. | ....... | 435/221 |
| 5,501,820 A | 3/1996 | Van den Bergh et al. | | |
| 5,567,601 A * | 10/1996 | Bryan et al. | ................. | 435/222 |
| 5,665,587 A * | 9/1997 | Aaslyng et al. | ............. | 435/221 |
| 5,700,676 A * | 12/1997 | Bott et al. | ................... | 435/221 |
| 5,741,664 A * | 4/1998 | Ballinger et al. | ........... | 435/68.1 |
| 5,741,694 A | 4/1998 | Hastrup et al. | | |
| 5,780,285 A * | 7/1998 | Ballinger et al. | ............ | 435/222 |
| 5,837,516 A * | 11/1998 | Ballinger et al. | ............ | 435/221 |
| 5,837,517 A * | 11/1998 | Sierkstra et al. | ............. | 435/221 |
| 6,121,226 A * | 9/2000 | Gosselink et al. | ........... | 510/400 |
| 6,245,901 B1 * | 6/2001 | von der Osten et al. | ..... | 530/402 |
| 6,287,841 B1 * | 9/2001 | Mulleners et al. | ........... | 435/221 |
| 6,300,116 B1 * | 10/2001 | von der Osten et al. | ..... | 435/220 |
| 6,312,936 B1 * | 11/2001 | Poulose et al. | .............. | 435/219 |
| 6,376,450 B1 * | 4/2002 | Ghosh et al. | ................. | 510/392 |
| 6,436,690 B1 * | 8/2002 | Brode et al. | ................. | 435/222 |
| 6,455,295 B1 * | 9/2002 | Brode et al. | ................. | 435/221 |
| 6,475,765 B1 * | 11/2002 | Brode et al. | ................. | 435/221 |
| 6,482,628 B1 * | 11/2002 | Poulose et al. | .............. | 435/221 |
| 6,555,355 B1 * | 4/2003 | Hansen et al. | .............. | 435/221 |
| 6,566,115 B1 * | 5/2003 | Weisgerber et al. | ......... | 435/221 |
| 6,599,730 B1 * | 7/2003 | Brode et al. | ................. | 435/221 |
| 6,610,642 B2 * | 8/2003 | Ghosh et al. | ................. | 510/392 |
| 6,673,590 B1 | 1/2004 | Poulose et al. | | |
| 6,727,085 B2 * | 4/2004 | Fano et al. | ................... | 435/220 |
| 6,815,193 B2 | 11/2004 | Poulose et al. | | |
| 6,831,053 B1 * | 12/2004 | Ghosh et al. | ................. | 510/392 |
| 6,838,425 B2 * | 1/2005 | Ghosh et al. | ................. | 510/392 |
| 6,902,922 B2 * | 6/2005 | Ness et al. | ................... | 435/219 |
| 6,927,055 B2 * | 8/2005 | Poulose et al. | .............. | 435/219 |
| 7,306,937 B2 * | 12/2007 | Poulose et al. | .............. | 435/219 |
| 7,332,320 B2 * | 2/2008 | Estell et al. | .................. | 435/219 |
| 2003/0157645 A1 * | 8/2003 | Kettling et al. | ............. | 435/69.1 |
| 2005/0181446 A1 * | 8/2005 | Roggen et al. | ............... | 435/7.1 |

FOREIGN PATENT DOCUMENTS

| | | |
|---|---|---|
| CN | 111395 A | 12/1995 |
| EP | 0 516 200 | 12/1992 |
| EP | 675196 | 10/1995 |
| GB | 2 271 120 | 6/1994 |

(Continued)

OTHER PUBLICATIONS

Siezen et al., "Homology Modelling and Protein Engineering Strategy of Subtilases, the Family of Subilisin-like Serine Proteinases", Protein Engineering, vol. 4, No. 7, pp. 719-737 (1991).

(Continued)

*Primary Examiner*—Nashaat T Nashed
*Assistant Examiner*—William W Moore
(74) *Attorney, Agent, or Firm*—Kristin J. McNamara

(57) ABSTRACT

The present invention relates to novel subtilase variants exhibiting alterations relative to the parent subtilase in one or more properties including: Wash performance, thermal stability, storage stability or catalytic activity. The variants of the invention are suitable for use in e.g. cleaning or detergent compositions, such as laundry detergent compositions and dish wash compositions, including automatic dish wash compositions.

13 Claims, 1 Drawing Sheet

FOREIGN PATENT DOCUMENTS

| | | |
|---|---|---|
| WO | WO 91/00335 | 1/1991 |
| WO | WO 91/00345 | 1/1991 |
| WO | WO 96/27671 | 9/1996 |
| WO | WO 96/28556 | 9/1996 |
| WO | WO 96/34935 | 11/1996 |
| WO | WO 96/34946 | 11/1996 |
| WO | WO 98/06279 | 2/1998 |
| WO | WO 98/20116 | 5/1998 |
| WO | WO 99/20726 | 4/1999 |
| WO | WO 99/20769 | 4/1999 |
| WO | WO 99/27082 | 6/1999 |
| WO | WO 99/49056 | 9/1999 |
| WO | WO 00/37599 | 6/2000 |
| WO | WO 00/37621 | 6/2000 |
| WO | WO 00/37658 | 6/2000 |
| WO | WO 00/71686 | 11/2000 |
| WO | WO 01/44452 | 6/2001 |
| WO | WO 02/22796 | 3/2002 |
| WO | WO 03/062380 | 7/2003 |

OTHER PUBLICATIONS

U.S. Appl. No. 10/481,723 Office Action (rejection for double patenting in light of subject application), 2008.

* cited by examiner

```
No:     1         10        20        30        40        50
a)  AQSVPYGVSQIKAPALHSQGYTGSNVKVAVIDSGIDSSHPDLKVAGGASM
b)  AQSVPWGISRVQAPAAHNRGLTGSGVKVAVLDTGI*STHPDLNIRGGASF

No:               60        70        80        90       100
a)  VPSETNPFQDNNSHGTHVAGTVAALNNSIGVLGVAPSASLYAVKVLGADG
b)  VPGEPST*QDGNGHGTHVAGTIAALNNSIGVLGVAPSAELYAVKVLGASG

No:              110       120       130       140       150
a)  SGQYSWIINGIEWAIANNMDVINMSLGGPSGSAALKAAVDKAVASGVVVV
b)  SGSVSSIAQGLEWAGNNGMHVANLSLGSPSPSATLEQAVNSATSRGVLVV

No:              160       170       180       190       200
a)  AAAGNEGTSGSSSTVGYPGKYPSVIAVGAVDSSNQRASFSSVGPELDVMA
b)  AASGNSG*AGS***ISYPARYANAMAVGATDQNNNRASFSQYGAGLDIVA

No:              210       220       230       240       250
a)  PGVSIQSTLPGNKYGAYNGTSMASPHVAGAAALILSKHPNWTNTQVRSSL
b)  PGVNVQSTYPGSTYASLNGTSMATPHVAGAAALVKQKNPSWSNVQIRNHL

No:              260       270  275
a)  ENTTTKLGDSFYYGKGLINVQAAAQ
b)  KNTATSLGSTNLYGSGLVNAEAATR
```

Figure 1

SEQUENCE LISTING

<160> NUMBER OF SEQ ID NOS: 2

<210> SEQ ID NO 1
<211> LENGTH: 275
<212> TYPE: PRT
<213> ORGANISM: B. amyloliquefaciens (subtilisin BPN')

<400> SEQUENCE: 1

```
Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
                20                  25                  30

Ser Gly Ile Asp Ser Ser His Pro Asp Leu Lys Val Ala Gly Gly Ala
            35                  40                  45

Ser Met Val Pro Ser Glu Thr Asn Pro Phe Gln Asp Asn Asn Ser His
        50                  55                  60

Gly Thr His Val Ala Gly Thr Val Ala Ala Leu Asn Asn Ser Ile Gly
    65                  70                  75                  80

Val Leu Gly Val Ala Pro Ser Ala Ser Leu Tyr Ala Val Lys Val Leu
                85                  90                  95

Gly Ala Asp Gly Ser Gly Gln Tyr Ser Trp Ile Ile Asn Gly Ile Glu
```

-continued

```
                    100                 105                 110
Trp Ala Ile Ala Asn Asn Met Asp Val Ile Asn Met Ser Leu Gly Gly
            115                 120                 125
Pro Ser Gly Ser Ala Ala Leu Lys Ala Ala Val Asp Lys Ala Val Ala
        130                 135                 140
Ser Gly Val Val Val Ala Ala Gly Asn Glu Gly Thr Ser Gly
145                 150                 155                 160
Ser Ser Ser Thr Val Gly Tyr Pro Gly Lys Tyr Pro Ser Val Ile Ala
                165                 170                 175
Val Gly Ala Val Asp Ser Ser Asn Gln Arg Ala Ser Phe Ser Ser Val
            180                 185                 190
Gly Pro Glu Leu Asp Val Met Ala Pro Gly Val Ser Ile Gln Ser Thr
        195                 200                 205
Leu Pro Gly Asn Lys Tyr Gly Ala Tyr Asn Gly Thr Ser Met Ala Ser
    210                 215                 220
Pro His Val Ala Gly Ala Ala Leu Ile Leu Ser Lys His Pro Asn
225                 230                 235                 240
Trp Thr Asn Thr Gln Val Arg Ser Ser Leu Glu Asn Thr Thr Lys
                245                 250                 255
Leu Gly Asp Ser Phe Tyr Tyr Gly Lys Gly Leu Ile Asn Val Gln Ala
            260                 265                 270
Ala Ala Gln
        275

<210> SEQ ID NO 2
<211> LENGTH: 269
<212> TYPE: PRT
<213> ORGANISM: B. lentus (subtilisin 309)

<400> SEQUENCE: 2

Ala Gln Ser Val Pro Trp Gly Ile Ser Arg Val Gln Ala Pro Ala Ala
1               5                   10                  15
His Asn Arg Gly Leu Thr Gly Ser Gly Val Lys Val Ala Val Leu Asp
                20                  25                  30
Thr Gly Ile Ser Thr His Pro Asp Leu Asn Ile Arg Gly Gly Ala Ser
            35                  40                  45
Phe Val Pro Gly Glu Pro Ser Thr Gln Asp Gly Asn Gly His Gly Thr
        50                  55                  60
His Val Ala Gly Thr Ile Ala Ala Leu Asn Asn Ser Ile Gly Val Leu
65                  70                  75                  80
Gly Val Ala Pro Ser Ala Glu Leu Tyr Ala Val Lys Val Leu Gly Ala
                85                  90                  95
Ser Gly Ser Gly Ser Val Ser Ser Ile Ala Gln Gly Leu Glu Trp Ala
                100                 105                 110
Gly Asn Asn Gly Met His Val Ala Asn Leu Ser Leu Gly Ser Pro Ser
            115                 120                 125
Pro Ser Ala Thr Leu Glu Gln Ala Val Asn Ser Ala Thr Ser Arg Gly
        130                 135                 140
Val Leu Val Val Ala Ala Ser Gly Asn Ser Gly Ala Gly Ser Ile Ser
145                 150                 155                 160
Tyr Pro Ala Arg Tyr Ala Asn Ala Met Ala Val Gly Ala Thr Asp Gln
                165                 170                 175
Asn Asn Asn Arg Ala Ser Phe Ser Gln Tyr Gly Ala Gly Leu Asp Ile
            180                 185                 190
```

```
Val Ala Pro Gly Val Asn Val Gln Ser Thr Tyr Pro Gly Ser Thr Tyr
        195             200             205

Ala Ser Leu Asn Gly Thr Ser Met Ala Thr Pro His Val Ala Gly Ala
    210             215             220

Ala Ala Leu Val Lys Gln Lys Asn Pro Ser Trp Ser Asn Val Gln Ile
225             230             235             240

Arg Asn His Leu Lys Asn Thr Ala Thr Ser Leu Gly Ser Thr Asn Leu
            245             250             255

Tyr Gly Ser Gly Leu Val Asn Ala Glu Ala Ala Thr Arg
        260             265
```

SUBTILASE VARIANTS

CROSS-REFERENCE TO RELATED APPLICATIONS

This application claims priority or the benefit under 35 U.S.C. 119 of Danish application nos. PA 2002 01705 and PA 2002 01933 filed Nov. 6, 2002 and Dec. 18, 2002, respectively, and U.S. provisional application nos. 60/427,156, 60/434,723, and 60/507,537 filed Nov. 18, 2002, Dec. 19, 2002, and Oct. 1, 2003, respectively, the contents of which are fully incorporated herein by reference.

BACKGROUND OF THE INVENTION

1. Technical Field

The present invention relates to novel subtilase variants exhibiting alterations relative to the parent subtilase in one or more properties including: Wash performance, thermal stability, storage stability or catalytic activity. The variants of the invention are suitable for use in e.g. cleaning or detergent compositions, such as laundry detergent compositions and dish wash compositions, including automatic dish wash compositions. The present invention also relates to isolated DNA sequences encoding the variants, expression vectors, host cells, and methods for producing and using the variants of the invention. Further, the present invention relates to cleaning and detergent compositions comprising the variants of the invention.

2. Description of Related

In the detergent industry enzymes have for more than 30 years been implemented in washing formulations. Enzymes used in such formulations comprise proteases, lipases, amylases, cellulases, as well as other enzymes, or mixtures thereof. Commercially the most important enzymes are proteases.

An increasing number of commercially used proteases are protein engineered variants of naturally occurring wild type proteases, e.g. Durazym®, Relase®, Alcalase®, Savinase®, Primase®, Duralase®, Esperase®, Ovozyme® and Kannase® (Novozymes A/S), Maxatase™, Maxacal™, Maxapem™, Properase™, Purafect™, Purafect OxP™, FN2™, FN3™ and FN4™ (Genencor International, Inc.). Further, a number of protease variants are described in the art. A thorough list of prior art protease variants is given in WO 99/27082.

However, even though a number of useful protease variants have been described, there is still a need for new improved proteases or protease variants for a number of industrial uses such as laundry or hard surface cleaning. Therefore, an object of the present invention is to provide improved subtilase variants for such purposes.

SUMMARY OF THE INVENTION

Thus, in a first aspect the present invention relates to a subtilase variant comprising at least a) an insertion, substitution or deletion of one of the amino acid residues K, H, R, E, D, Q, N, C, V, L, I, P, M, F, W, Y, G, A, S, T in one or more of the positions 62, 68, 97, 98, 99, 106, 131, 170, 245, 252, in combination with at least one of the following modifications

*0AQSVPWG; A1T,V; Q2L; S3T,A,L; V4L,A; I18V,T; S9G, D,R,K,L,V; R10H,K; V11A; Q12D; A13V; P14S,T,D,A,M, V,K,Q,L,H,R,I; A15M,T; A16P; H17R; N18S,H; R19W,K,L, F,G,I; G20*,R,A; L21F,LP,LW,LA,LG; T22S,A,K,TV,TG, TL,TW,TV,G,L,TY; G23S; S24P; K27R,V28I; V30I; I35T,V; T38S; P40L; N43D; R45H,K; G46D; A48T; S49N; F50S; V51A,I,D; P52V,A; P55S,A; S57P; G61E,D,S,R,GP; N62D, ND,NE,DE,NG,E,S; V68A,S,L,I; T71A; I72V; L75I; N76S, D; N77S; S78T; V81A; A85T; S87C; A88V,T; E89G; K94N; V95C,T; L96LA,LG; G97E,D,W,A,GG,GA,GV,N,GS; A98S,D,E,T,AS,AD,AV,AE,AH,Q,N,M,L,G,R,V,S; S99D, L,A,AD,SD,SM,SG,DA,P,G,N,C,M,V,I; G100S,GE,C; S101SA, SK; G102D,S; S103D,E,Y,L,Q,H,T; V104T,S,R,I, N,M,L,D; S106D,E,T,M,G,A,L,F,I; I107T,V,M; A108V,T,S; L111I,V; A114V; N116S,D; G118D; M119L,I,V,A,S; H120N,D,Q,K,E,Y,S; V121A; L124C; L126I; G127E; S128N,I,G,C; P129PSN,T,E,D,S,N,A; S130P,T,C,*; P131M, F,W,L,A,H,T,*,PA,S,Q,R,E,G,D,C; S132G,T; A133ASA; T134A; Q137H,E,D; A138G,V; V139L,I; N140D, K; T143A; S144D, N,P; R145G; V150I; A151V,G; A152P; A158T,V,C,E,L,D, M; G160A,D; S163G,C,N,A; Y167K,A, I; A168G; A169G; R170C,S,H,L; Y171C; A172V; N173D; A174V; M175L,I,V,A,S,T; N183D; N184D,S; N185S,D; R186L,C,H; S188G; S190A; Y192H; G195F,E; V203S,A,L, Q,M, F,I; N204T,D,S; Q206L; Y209C,H; G211D; S212N,L; T213A; Y214C,H; A215D,T; N218D,S; M222L,I,V,A,S; A223G; T224A,S; A228T; A230V; A232S,L,T,P; V234I; Q236A,L,D,T,C,M,F,S; K237R; N238D; P239T,S; S240F; S242T; V244I,M,A; Q245R,K,E,D,T,F,N,V,W,G,I,S,C,L,A, M; N248P,D,S; K251E,R; N252G,H,D,V,M,S,T,E,Y,S,Q,K, A,L; A254S; T255A,S; S256N,R,G; L257G; G258K, S259A, N,G; T260A,R; N261D; L262S, Q,V; Y263H,F; G264E; S265G,R,N; V268L,I; N269T; N296K; E271A; T274S,L, A,R or b) one of the following combination variants A108T+L111V; L124I+S125A; P129S+S130AT; L96LA+ A151G+V203A; S49N+V203L+N218D; S3T+A16P+ R45C+G100S+A230V; I8V+R19K+V139I; N76D+ A174AL+A194P+A230V; N185R; N62NE; H120Q+ Q137E, G61GE, G61GS, G100L, A133D, V68A, N123D, L111F+Y263H, V11A+G61GE+V227A+S240F, A133E+ S144K+N218D, S128A+P129S+S130SP, S9R+A15T+ T22TQ+S101P, S9R+A15T+H120R+Q137D+N173S, G97E, Q245W, S9R+A15T+L96LG+Q137E+Y209H, S9R+ A15T+L111V+Q137E+G211D, S9R+A15T+L111I+ Q137E, S9R+A15T+L111I+H120N+Q137E, S9R+A15T+ L96LG+H120Q+Q137E, S9R+A15T+T260M, S9R+A15T, Q245I, S9R+A15T+H120G+Q137E+N218D, S9R+A15T+ S130P, Q245F, S9R+A15T+N218D, G63E+N76D+A194P+ A230V, S9R+A15T+T224A, G100S, S9R+A15T+D60DG, A138V+V139I+A194P+N218D+A230V, A108V+A169G+ R170A+Y171H, I8V+P14L+R19L+V30I+I35V+S57P+ P129S+Q137D+S144D+S256N, A133D+T134S+Q137A, Q137D, A98AH, V51D, Q12E+P14L+A15T, G63E+N76D+ A194P+A230V, Q12E+P14L+A15T, G97GS or c) one or more modifications in position 68, wherein said modification(s) comprise(s): deletion, insertion and/or substitution of an amino acid residue selected from the group consisting of K, H, R, E, D, Q, N, C, V, L, I, P, M, F, W, Y, G, A, S and T.

In a second aspect the present invention relates to a subtilase variant comprising a) the combination of one or more of the modifications X62D,XD,XE,XG,DE
X68A,S,L,I
X97E,D,W,A,N,XG,XA,XV,XS
X98S,D,E,T,XS,XD,XV
X99D,L,A,P,G,N,AD,XD,XM,XG,DA
X106D,E,T,M,G,A,L,F,I X131M,F,W,L,A,H,T,*,S,Q,R,E,G,XA
X170C,S,H
X245R,K,E,D,T,F,N,V,W,G,I,S,C,L,A
X252G,H,D,V,M,S,T,E,Y,S,Q,K with at least one of the following modifications

*0AQSVPWG; A1T,V; Q2L; S3T,A,L; V4L,A; I8V,T; S9G, D,R,K,L,V; R10H,K; V11A; Q12D; A13V; P14S,T,D,A,M, V,K,Q,L,H,R,I; A15M,T; A16P; H17R; N18S,H; R19W,K,L, F,G,I; G20*,R,A; L21F,LP,LW,LA,LG; T22S,A,K,TV,TG, TL,TW,TV,G,L,TY; G23S; S24P; K27R,V28I; V30I; I35T,V; T38S; P40L; N43D; R45H,K; G46D; A48T; S49N; F50S; V51A,I,D; P52V,A; P55S,A; S57P; G61E,D,S,R,GP; N62D, ND,NE,DE,NG,E,S; V68A,S,L,I; T71A; 172V; L75I; N76S, D; N77S; S78T; V81A; A85T; S87C; A88V,T; E89G; K94N; V95C,T; L96LA,LG; G97E,D,W,A,GG,GA,GV,N,GS; A98S,D,E,T,AS,AD,AV,AE,AH,Q,N,M,L,G,R,V,S; S99D, L,A,AD,SD,SM,SG,DA,P,G,N,C,M,V,I; G100S,GE,C; S101SA, SK; G102D,S; S103D,E,Y,L,Q,H,T; V104T,S,R,I, N,M,L,D; S106D,E,T,M,G,A,L,F,I; I107T,V,M; A108V,T,S; L111I,V; A114V; N116S,D; G118D; M119L,I,V,A,S; H120N,D,Q,K,E,Y,S; V121A; L124C; L126I; G127E;
S128N,I,G,C; P129PSN,T,E,D,S,N,A; S130P,T,C,*; P131M, F,W,L,A,H,T,*,PA,S,Q,R,E,G,D,C; S132G,T; A133ASA; T134A; Q137H,E,D; A138G,V; V139L,I; N140D, K; T143A; S144D,N,P; R145G; V150I; A151V,G; A152P; A158T,V,C,E,L,D, M; G160A,D; S163G,C,N,A; Y167K,A, I; A168G; A169G; R170C,S,H,L; Y171C; A172V; N173D; A174V; M175L,I,V,A,S,T; N183D; N184D,S; N185S,D; R186L,C,H; S188G; S190A; Y192H; G195F,E; V203S,A,L, Q,M, F,I; N204T,D,S; Q206L; Y209C,H; G211D; S212N,L; T213A; Y214C,H; A215D,T; N218D,S; M222L,I,V,A,S; A223G; T224A,S; A228T; A230V; A232S,L,T,P; V234I; Q236A,L,D,T,C,M,F,S; K237R; N238D; P239T,S; S240F; S242T; V244I,M,A; Q245R,K,E,D,T,F,N,V,W,G,I,S,C,L,A, M; N248P,D,S; K251E,R; N252G,H,D,V,M,S,T,E,Y,S,Q,K, A,L; A254S; T255A,S; S256N,R,G; L257G; G258K, S259A, N,G; T260A,R; N261D; L262S,Q,V; Y263H,F; G264E; S265G,R,N; V268L,I; N269T; N296K; E271A; T274S,L,A, R.

In a third aspect the present invention relates to a subtilase variant comprising at least one of the alterations disclosed in Table I below:

TABLE I

| subtilase variants of the inventions having one or more of the alterations: | |
|---|---|
| G97E + A98S | V28I + A98AD + T224S |
| G97D + A98D | S99AD + M175V + P131F |
| V95C + G97W + A98E | S99AD + P131L |
| V95T + G97A + A98D | S9R + S99AD + P131W |
| S103Y + V104M + S106D | V68A + N116S + V139L + Q245R |
| V104T + S106D | S3T + A16P + R45C + G100S + A230V |
| S3T + A16P + S99SD + S144D + A158T + A230V + T260R | I8V + S9R + A15T + R19W + V30I + G61D + S99SD + S256N |
| S103D + V104T + S106T | V30I + S99SD + S256R |
| S103D + V104L + S106M | G61S + S99SD + V244I |
| S103D + V104T + S106G | V68A + V139L + S163G + N185S |
| S103D + V104S + S106A | S99SD + Y263H |
| S103H + V104N + S106D | V104N + S106T |
| S103E + V104I + S106T | S99SG + S144D |
| S103Q + V104T + S106E | V30I + S99SD |
| S103E + S106T | N18H + S99SD |
| S103E + V104R + S106A | S9R + T22S + S99SD + K251E |
| A108T + L111V | A48T + V68A + P131M |
| L124I + S125A | A15M + S99SM + V139I + V244I |
| L124C + P131* | P14T + A15M + S99SD |
| P129S + S130AT | I8V + S99SD + S144D + A228T |
| L96LA + A151G + V203A | I8V + R19K + V139I |
| S99SD + A108V + V139L | I35T + N62D |
| S99SD + S190A | N62D + S265G |
| S99SD + V203A | Q2L + N62D |
| S99SD + V139I | N62D + N76D |
| S99SD + A108V | R45H + G61E + V68A |
| S99SD + S106A + A151G | N62D + V121A |
| V68A + S106A | N62D + A215D |
| V68A + N185D + V203S | N62D + N238D |
| V68A + V139L | N62D + R145G |
| V68A + V139I | V4L + N62D + E89G |
| V68A + A158V | N62D + S188G + K251R |
| V68A + V203A | S49N + N62D |
| V68A + V203S | N62NE |
| V68A + V203L + S259A | V11A + N62DE |
| V68A + S106L | N62ND + N184S + S256G |
| V30I + V68A + V203S | N18S + N62D + I107T + A254S |
| V51A + V68A + S106T + A168G | S57P + N62ND |
| V51A + V68A + S106T + A168G | N62NE + V234I |
| V68A + N76S + V203M + P239T | Q137H + R170C + G195E |
| V68A + V203L | S99A + S101SA |
| V68A + L75I + V203Q | R10K + P14A + R19K + A98AS + S128N |
| V68A + T71A + V139L | T22A + R45K + A98AS + S128N |
| Y192H + V68A | A98AV + S99D + Y167K |
| V68A + S106A + A108T | S9G + P14K + Y167A + R170S |
| V68A + S106T + A108T | S9D + P14T + Y167A + R170S |
| V68S + A108S | S9R + P14M + A98AD |

TABLE I-continued subtilase variants of the inventions having one or more of the alterations:

| | |
|---|---|
| V68A + N76S + G211D | S9R + R19L + A98AD + E271A |
| V68A + S106T + A108T | S9R + P14S + R19F + A98AD |
| A151V + R170C | S99DA + P129PSN + P131A |
| P14D + A98AS + H120D + G195F + S212N + M222S | S99AD + V244M + Q245K + N248D + K251R + T255A + S256N |
| S49N + V203L + N218D | S9R + P14V + R19G + A98AD |
| V68A + S106M + N184D | S99AD + N248P + T255A + S256G |
| P55S + V68L + A158E + G160A | *0AQSVPWG + A98AD |
| V68A + A158C | T22A + S99AD |
| V68A + A158L + Y214C | K94N + A98T + S99L |
| A88V + S99AD + P131F | N76D + A174AL + A194P + A230V |
| P14T + A16P + I72V + S99SD + V244I + T260A | P40L + N218D + A232S + Q236L + Q245E + S259N |
| S99AD + P131F | A232L + Q236D + Q245E |
| R10H + N62D | A232T + Q236L + Q245D |
| V28I + A98AD + T224S | R170H + Q236A + Q245R |
| S9K + T22K + S99AD | A232L + Q236T + Q245D |
| P14S + S99AD + P131W | G97GG + P131H + Q137E + V268L |
| V68A + I72V + P131F | A88V + G97GV + P131H |
| S9R + S99AD | G97GA + H120Q + S130P + G264E |
| S9K + S99AD | G97GG + V139L |
| V28I + A88V + G100S + P131M | G97GG + Q137D |
| S103L + V104S + S106G | G97GG + H120D + Q137H |
| V68A + T224A | N185R |
| V68A + P131F | P131H + Q137E |
| A48T + V68A + P131M | V104I + H120N + P131H + Q137E |
| V68A + I72V + P131F | H120Q + Q137E |
| G100GE + P131F | S9R + A15T + G97GV + H120D |
| S99AD + P131F + T260A | G100S + H120Q + Q137H |
| R19G + A98AS | V68A + H120K + Q137E |
| G61R + N62D | G97GA + H120E |
| V68A + S106M + N184D | H120D + S128I + Q137D |
| P55S + V68L + A158E + G160A | G97GG + P131H |
| V68A + A158C | G97GG + H120N + L126I |
| R19W + G61S + S99SD + N204T + Y263H + S265R | S9R + A15T + G97GA + H120D + P131H + Q137E |
| A232T + Q236C | S9R + A15T + G97GV + P131H + Q137H |
| N62D + A232T + Q236C | S9R + A15T + G20* + L21F + N62D + Q245N |
| A232P + Q236L + Q245E | S9L + A15T + T22TV + V139L + Q245F |
| A232S + Q236L + Q245T + K251E | S132G + Q245F |
| S163C + Q236M + Q245T + S256G | S9R + A15T + T22TG + N62D + V139L + Q245V |
| N218D + A232L + Q236F + Q245F | S9L + A15T + T22TV + V139L + Q245F + L262S |
| S163N + A232L + Q236S + Q245E | S9R + A15T + T22TL + N62D + Q245W |
| A232S + Q236S + Q245E | V68A + A158L + Y214C |
| V68A + V203L | N62D + V150I |
| V68S + A158D | S3T + P14Q + A15M + R19K + N62D + S144D |
| I8V + A15T + R19K + A85T + S99SD + A114V + V244I + S256N + Y263H | P14Q + R19W + V51I + G61E + S99SD + V139I + T260R |
| L111F + Y263H | S3T + P14L + H17R + S99SD + V139I + S144D |
| P52V + S78T + S99SD | S3A + V30I + S99SD + S106G + N248S |
| A15M + S99SD + V268I | I8V + A15T + S99SD |
| S99G + S128N + N183D + A232L + Q236T + Q245R | S3T + S9R + P14H + A15M + R19L + S99SD + V139I |
| S99R + S101SA | S9R + A15T + G97GG + H120D + Q137E |
| L96LA + A98T + P131AA | S9R + A15T + G20A + G97GV + H120D + P131H |
| A98E + S99P | S163N + A232L + Q236A + Q245G |
| V28I + S99AD + P131F | N173D + A232L + Q236A + Q245N |
| S9R + A15T + G97GV + Q137H | P55S + V68A + S106M + A108T + P129T |
| V81A + P131T + A133S + Q137E | K27R + V68L + G118D + A158E |
| N43D + V68A + S106F + N238D | A98E + S99A + S101SK |
| V68A + V203F | V68A + N140D + T143A + S144N |
| V68A + S106E | N62D + N140K + T143A + S144D |
| V68A + S106I | S9F + P14T + R19L + A98AD |
| V68A + A158M + R170C | S9V + P14R + R19F + A98AD |
| V68A + P129T + N218D | S99A + S99SD + G258K + L262Q |
| V68S + P129E | S87C + S99SA + S99D + P131A |
| V68S + P129D | S99A + S99SD + G258K + L262Q |
| V68L + P129E + N261D | V28I + S99A + *99aD + P131F |
| G97GV + H120D | A85T + G102D + S106T + K237R |
| P131A + A133ASA | V68A + T71A |
| L111F + Y263H | G61GS |
| V11A + G61GE + V227A + S240F | G100L |
| A133E + S144K + N218D | A133D |
| S128A + P129S + S130SP | V68A |
| G61GE | N123D |
| S9R + A15T + T22TW + N204D + Q245I | Q245W + N252V |
| S9R + A15T + G97GG + P131S + Q137H | R45H + Y171C + Q245W + N252S |
| S9R + A15T + T22TG + N62D + V139L + Q245G | G20R + A48T + R170C + Q245W + N252Q |
| S9R + A15T + T22TL + N62D + I107V + V139L + Q245W | S9R + A15T + A16P + G97GA + P131S + Q137D + N204S |

TABLE I-continued subtilase variants of the inventions having one or more of the alterations:

S9G + A15T + G97GA + Q137H
S9R + A15T + V68A + Q245R
S9R + A15T + G97GA + H120N + S212L
S9R + A15T + L96LG + H120D + P131H + R186L
S9R + A15T + G97GA + H120D + Q137D
N62D + N252T
V4A + S9R + A15T + G97GV + H120D
S9R + A15T + G97GV + H120D + Q137H
S9R + A15T + L96LG + H120N + P131H + Q137E
S9R + A15T + L96LG + H120D + P131S + Q137E
S9R + A15T + H120N + P131T + N218D
S9R + A15T + L21LP + T22TV + M119I + N218D + Q245I
S9R + A15T + L96LG + H120D + G160D
V68A + S106A + G118D + Q245R + T255S + L257G + T274L
S9R + A15T + G61E + A85T + P239L + Q245C
S9R + A15T + P131H + S144P
S9R + A15T + G97GA + Q137E
S9R + A15T + G97GA + H120Q + P131H + Q137E
S9R + A15T + L21LW + G100S + V139L + Q245V
S9R + A15T + G97GA + Q137H + N218S
S9R + A15T + L96LG + H120N + P131S + Q137H
S9R + A15T + G97GA + H120N + Q137E
S9R + A15T + L96LG + P131T + Q137H
S9R + A15T + L96LG + H120N + P131S
S9R + A15T + V68A + Q137D
S9R + A15T + G97GA + H120Y + Q137H
S9R + A15T + G97GA + Q137D
S9R + A15T + K94N + H120N + P131H
S9R + A15T + L96LG + P131H + Q137D
S9R + A15T + F50S + H120D + P131H
S9R + A15T + G97GA + H120N + Q137D + N248D
S9R + A15T + L96LG + P131Q + Q137D
S9R + A15T + T22G + V139L + Q245L
V139L + Q245R
S9R + A15T + Q245F
S9R + A15T + Q245S
S9R + A15T + G97GV + H120Q
S9R + A15T + G97GA + Q137E + L262V
S9R + A15T + G127E + P131R + Q137H
S9R + A13V + A15T + I35V + N62D + Q245F
S9R + A15T + Q245V
V139L + Q245F
S9R + A15T + T22A + V139L + Q245E
S9R + A15T + T22L + V139L + Q245V + A254S
S9R + R19L + A98AD
P14R + A98AD
S9R + A15T + Q245L
S9R + A15T + G61E + A85T + P239S + Q245V
S9R + A15T + G61E + A85T + Q206L + Q245R
P239T + Q245R
S9R + A15T + N62NG + Q245T
S9R + A15T + G61GP + Q245L
S9R + A15T + G61E + A85T + Q137H + Y209C + Q245G

S9R + A15T + G61E + A85T + P239S + Q245C
V68I + A98AD
V68A + N269K
N62D + Q245A + N252G + S265G
N218D + Q245G + N252H
S9R + A15T + G102S + M175T + Q245R + N252D
S9R + A15T + N62D + Q245W + N252V
S9R + A15T + N62D + Q245R + N252M
S9R + A15T + N62D + Q245W + N252S
S99SD + N204S + Q245R
N62D + Q245R
N62D + A151G
V68A + S106T
S99A + S99SD + V203L
A98AD + A215T
N62D + Q245G + N252T
A152P + Q245R + N252T
S163N + T213A + Q245R
S106L + Q245R + N252E
S9V + P14R + R19F + A98AD
S9R + A15T + L111I + Q137E
S9R + A15T + G97GA + Q137E
S9R + A15T + L96LG + Q137E + Y209H

N218D + Q245W + N252E
G20R + R170C + Q245R + N252V
S9R + P14I + R19K + A98AD + T274S
A98AE + V203I
V51A + V68A + S163G + V203A
N62D + Q245W + N252H
N62D + Q245W + N252A
G20R + N62D + V244I + Q245W + N252E
N204D + Q245S
N62D + Q245W + N252E
N62D + Q245R + N252V
S9R + A15T + S24P + G61E + A85T + P239S + Q245A
G102S + M222S + Q245L + N252D
A15M + V30I + N62D + S99N + L111I + V244A + S265N
S9R + A15T + T22TG + N62D + V139L + Q245S
S3T + Q12D + R19W + V30I + S106G + I107M
V68A + A88T + V139L
V51I + L111I + G118D + Q245R
V68A + V203L
A1T + V68A + N116D + G118D
V68A + G118D + Q245R
N62D + V139I + N183D + N185S + V203I + Q245R + L262S
N62D + I72V
N62D + V81A + Q245R
T22A + V68A + S106T + G118D
V68A + L111I + V203I
G61E + V68A + A169G
V68A + L111V
V68A + G118D + V203A + K251R
V68A + G118D
A1V + V51A + V68A + V203I
V68A + V139L + A223G
N62D + Y214H + K237R
V68A + S106A + G118D + Q245R
S9R + A15T + T22A + N62D
A98Q + S99D
S9R + P14I + R19K + A98AD
S9R + A15M + A16P + T22S + S99AD
S99AD + T255R + S256N
S9R + A15T + T22TQ + S101P
S9R + A15T + H120R + Q137D + N173S
G97E
Q245W
S9R + A15T + L96LG + Q137E + Y209H
S9R + A15T + L111V + Q137E + G211D
S9R + A15T + L111I + Q137E
S9R + A15T + L111I + H120N + Q137E
S9R + A15T + L96LG + H120Q + Q137E
S9R + A15T + T260M
S9R + A15T
Q245I
S9R + A15T + H120G + Q137E + N218D
I8V + P14L + R19L + V30I + I35V + S57P + P129S + Q137D + S144D + S256N
Q245F
S9R + A15T + N218D
G63E + N76D + A194P + A230V
S9R + A15T + T224A
G100S
S9R + A15T + D60DG
A138V + V139I + A194P + N218D + A230V
A108V + A169G + R170A + Y171H
S9R + A15T + S130P
A133D + T134S + Q137A
Q137D
A98AH
V51D
Q12E + P14L + A15T
G63E + N76D + A194P + A230V
Q12E + P14L + A15T
G97GS
Q245W + N252Y
A169G + R170H
Q12E + P14L + A15T
P14R + A98AD
G100S
A169G + R170H

TABLE I-continued subtilase variants of the inventions having one or more of the alterations:

S9R + A15T + L96LG + H120N + P131S
S9R + A15T + G97GV + H120Q
S9R + A15T + L96LG + H120Q + Q137E
S9R + A15T + G97GV + P131S
S9R + A15T + K94N + H120N + P131H
S9R + A15T + N76S + L111V + P131H + Q137D
S9R + A15T + F50S + H120D + P131H
S9R + A15T + L96LG + S130*
S9R + A15T + T22TL + N62D + I107V + V139L + Q245W
S9R + A15T + G97GA + H120D + Q137H + M222V
S9R + A15T + G97GA + H120N + Q137D + N248D
S9R + A15T + L21LW + G100S + V139L + Q245V
S9R + A15T + G20* + L21F + N62D + Q245N
S9R + A15T + L21LC + V139L + R186H + Q245M
S132G + Q245F
S9R + A15T + T22TG + N62D + V139L + Q245G
S9R + A15T + L96LG + P131Q + Q137D
S9R + A15T + T22TQ + S101P
S9R + A15T + T22TG + N62D + V139L + Q245V
S9R + A15T + T22TL + N62D + Q245W
S9R + A15T + T22TW + N204D + Q245I
S9R + A15T + T22TG + N62D + V139L + Q245S
S9R + A15T + S130P
Q245W
S9R + A15T + L21LP + T22TY + V139L + G160D + Q245L
S9R + A15T + G61E + A85T + P239L + Q245C
S9R + A15T + L21LP + T22TV + M119I + N218D + Q245I
S9R + A15T + V68A + Q245R
S9R + A15T + T22A + V139L + Q245E
V139L + Q245R
S9R + A15T + Q245F
S9R + A15T + Q245S
S9R + A15T + T260M
S9R + A15T
S9R + A15T + L21LG + T22TV + V139L + N204D + Q245N
V139L + Q245F
S9R + A15T + T22G + V139L + Q245L
S9R + A15T + Q245V
Q245F
S9R + Q245C
S9R + A15T + N218D
S9R + A13V + A15T + I35V + N62D + Q245F
S9R + A15T + T224A
S163N + A232L + Q236A + Q245G
S9R + A15T + A16P + G97GA + P131S + Q137D + N204S
N218D + A232L + Q236F + Q245F
S163N + A232L + Q236S + Q245E
G97GA + H120E
G97GG + P131H
S9R + A15T + G97GA + H120D + P131H + Q137E
S9R + A15T + G97GV + Q137H
S9R + A15T + G97GV + H120N
S9R + A15T + G97GG + P131S + Q137H
S9R + A15T + G97GG + H120N + Q137D
S9R + A15T + H120Q + P131C + Q137H
S9R + A15T + G97GV + H120D + Q137H
S163C + Q236M + Q245T + S256G
S9R + A15T + G97GG + H120D + P131H + Q137H
S9R + A15T + G97GV + H120E + Q137H
S9R + A15T + G97GV + P131T + Q137H
S9R + A15T + G97GV + H120Q + Y263F
S9R + A15T + G97GV + S106A + P131H
S9R + A15T + G97GG + L111I + P131T + Q137H
S9R + A15T + G97GV + P131H + Q137H
S9R + A15T + G20A + G97GV + H120D + P131H
S9R + A15T + G97GA + H120D + P131S + Q137E
S9G + A15T + G97GA + Q137H
S9R + A15T + H120R + Q137D + N173S
S9R + A15T + L96LG + H120N + P131H + Q137E
S9R + A15T + L96LG + H120D + P131S + Q137E
S9R + A15T + H120N + P131T + N218D
S9R + A15T + G97GA + H120D + Q137D
S9R + A15T + L96LG + H120D + P131H + R186L
S9R + A15T + G97GA + R186C
V4A + S9R + A15T + G97GV + H120D
S9R + A15T + L96LG + H120D + G160D
S9R + A15T + G97GA + H120N + S212L
A98AD + A169G
A138V + V139I + A194P + N218D + A230V
S99A + S99SD + V203L
V68A + S106T
A98AD + A215T
A108V + A169G + R170A + Y171H
S3L + N62D + S163A + S190A
S9R + P14I + R19K + A98AD + T274S
S9R + A15T + G61E + A85T + N218D + P239S + Q245L
S9R + A15T + S24P + G61E + A85T + P239S + Q245A
S99SD + P131F
N62D + P131F + A172V
N62D + P131F
V68A + A88T + V139L
V68A + G118D + V203A
P40L + V68A + A108T + A138V + V203I
I8T + A98AD + T274R
A98AE + V203I
V51A + V68A + S163G + V203A
A1V + V51A + V68A + V203I
V68A + G100S
V68A + V203L
A1T + V68A + N116D + G118D
N62D + A169G + V203I + Q245R
G23S + S99SD + A194P + S242T + Q245R + T274R
S99SD + N204S + Q245R
N62D + V139I + N183D + N185S + V203I + Q245R + L262S
V68A + S106A + G118D + Q245R
V51I + L111I + G118D + Q245R
N62D + Q245R
N62D + I72V
S9R + R19L + A98AD
S9G + P14R + R19I + A98AD
S9R + A15T + T22L + V139L + Q245V + A254S
S99G + S128N + N183D + A232L + Q236T + Q245R
S9R + A15T + Q245L
S9R + A15T + N62NG + Q245T
S9R + A15T + N62ND + V139L + Q245E
S9R + A15T + N62ND + V139L + N261D
Y167I + R170L + Q245E
Y167I + R170L + Q245R
Y167I + R170L + Q245M
Y167I + R170L
S99SE + Q245R
S9R + A15T + G61E + A85T + Q137H + Y209C + Q245G
S9R + A15T + G61E + A85T + P239S + Q245C
G102S + M222S + Q245L + N252D
N62D + Q245A + N252G + S265G
N62D + Q245G + N252T
S9R + A15T + N62D + Q245W + N252V
S9R + A15T + N62D + Q245R + N252M
S9R + A15T + N62D + Q245W + N252S
S163N + T213A + Q245R
S106L + Q245R + N252E
Q245W + N252Y
Q245W + N252V
G20R + A48T + R170C + Q245W + N252Q
N62D + N252T
N218D + Q245W + N252E
G20R + R170C + Q245R + N252V
N62D + Q245W + N252H
N62D + Q245W + N252A
G20R + N62D + V244I + Q245W + N252E
N204D + Q245S
N62D + Q245W + N252E
N62D + Q245R + N252V
A98L + S99C + Q245R
N62D + A98R + Q245R
S9R + A15T + V68A + S99G + Q245R + N261D
S9R + A15T + G20* + L21F + N62D + Q245R
S9R + A15T + G20* + L21F + N62E + Q245R
V68I + A98AD
S9R + A15T + H120D + Q137D
S9R + A15T + N77S + L96LG + H120D + P131Q
S9R + A15T + G97GA + H120N + Q137E
S9R + A15T + G97GA + Q137E + L262V
S9R + A15T + P131H + S144P

TABLE I-continued subtilase variants of the inventions having one or more of the alterations:

| | |
|---|---|
| S9R + A15T + G97GA + Q137H + N218S | S9R + A15T + G127E + P131R + Q137H |
| M222S + Q245G + N252G | S9R + A15T + V68A + S99G + Q245R + N261D |
| V68I + V203L | N62D + P131F + A172V |
| V51A + S163T | N62D + P131F |
| S106A + A138G | S99SD + Q245R |
| V139I + A151G | S9R + A13T + S99A + S99SD + P131F |
| A98R + G100C + Q245R | S9R + A15T + N62S + H120N + P131T + N218D |
| S9R + A15T + S99G + G100S + H120N + P131S + Q137H | S9R + A15T + S99C + H120N + P131S + Q137H + M222S |
| A15T + N185D + M222S + Q245R + N252V | A98G + S99C + Q245R |
| S9R + A15T + T22TL + G61E + L96LG + Q137D + Q245R | A98T + S99G + G100S + S240F + Q245R |
| S9R + T22TL + G61E + G97GG + M119I + P131T | S9R + A15T + H120N + P131T + N218D + N269T |
| Y209H + M222S + Q245G + N252L | M222S + Q245M + N252E |
| S9R + A15T + G61E + H120S + Q137D + V139L + N218D | S9R + A15T + L96LG + H120N + P131S + Q137H + M222S |
| S9R + A15T + N62D + H120N + P131T | S9R + A15T + G61E + A98S + S99M + Q245R |
| S9R + A15T + V68A + N218D + Q245R | A98G + G100S + Q245R + N261D |
| S9R + A15T + V68A + H120N + N218D + Q245R | S9R + A15T + V68A + A98L + Q245R |
| S9R + A15T + V68A + A174V + Q245R | S9R + A15T + V68A + A98G + S99V + Q245R |
| S9R + A15T + G46D + V68A + N218D + Q245R | S9R + A15T + V68A + A98M + Q245R + N248D |
| G97D + A98N + S128G + S130T + P131D + T134A | S9R + A15T + G61E + V68A + A98S + S99G + Q245R |
| S9R + A15T + V68A + A98M + S99G + Q245R + T274A | S9R + A15T + A88V + A98R + S99G + G100C + H120N + P131S + Q137H |
| S9R + A15T + V68A + A98L + S99G + Q245R | A98V + S99C + Q245R |
| S9R + A15T + A98G + S99C + H120N + P131S + Q137H | S9R + A15T + G20* + L21F + G61E + *61aP + Q245R |
| S9R + A15T + T38S + A98R + S99C + G100S + H120N + P131S + Q137H | S9R + A15T + V68A + A98G + S99I + K237R + Q245R |
| S9R + A15T + A98C + G100S + H120N + P131S + Q137H | S9R + A15T + V68A + H120N + P131S + Q137H + Q245R |
| S9R + A15T + A98S + G100S + H120N + P131S + Q137H | S9R + A15T + V68A + H120D + P131S + Q137H + Q245R |
| S9R + A15T + G20* + L21F + N62D + Q245R | A98S + S99G + G100S + Q245R |
| S9R + A15T + G20* + L21F + N62D + Q245R + S259G | S9R + A15T + A98S + S99G + G100S + H120N + P131S + Q137H |
| A98S + G100S + Q245R | A98T + S99G + G100S + Q245R |
| S9R + A15T + G20* + L21F + *61aA + V68A + Q245R | S9R + A15T + G20* + L21F + P52T + N62D + Q245R |
| S9R + A15T + G20* + L21F + N62E + Q245R | A98L + S99C + Q245R |
| V68A + S105G + S106A | V68A + S106A + T213A |
| S9R + A15T + Y167I + R170L | S9R + A15T + V68A |
| V68A + S106A + N252M + Y263C | V68A + S106A + Q245W |
| V68A + S106A + Q245R + N252D | V68A + S106A + Q245W + N252K |
| V68A + S106A + A174V + Q245R + N252D | S9R + A15T + V68A + Q245R + N252S |
| S9R + A15T + V28I + V68A + Q245R + N252A | S9R + A15T + V68A + A194T + Q245R + N252E |
| S9R + A15T + G20* + L21F + *63aG + Q245R + N272V | S9R + A15T + G20* + L21F + *62aS + N218D + Q245R |
| S9R + A15T + G20* + L21F + *61aS + V68A + G160D + Q245R | S9R + A15T + V68A + H120N + P131S + Q137H + Q245M | wherein
(a) the variant of Table I exhibits protease activity, and
(b) each position corresponds to a position of the amino acid sequence of subtilisin BPN', shown in FIG. 1 and SEQ ID NO: 1.

In a fourth aspect the present invention relates to an isolated polynucleotide encoding a subtilase variant of the invention.

In a fifth aspect the present invention relates to an expression vector comprising the isolated polynucleotide of the invention.

In a sixth aspect the present invention relates to a microbial host cell transformed with the expression vector of the invention.

In a seventh aspect the present invention relates to a method for producing a subtilase variant according to the invention, wherein a host according to the invention is cultured under conditions conducive to the expression and secretion of the variant, and the variant is recovered.

In an eighth aspect the present invention relates to a cleaning or detergent composition, preferably a laundry or dish wash composition, comprising the variant of the invention.

In a ninth aspect the present invention relates to a subtilase variant comprising at least one of the alterations disclosed in Table II below:

TABLE II subtilase variants of the inventions having one or more of the alterations:

| | |
|---|---|
| G97GA + H120D + P131H + Q137E | L111I + Q137E |
| G97GV + Q137H | G97GA + Q137H + N218S |
| T22TQ + S101P | L96LG + H120N + P131S + Q137H |
| G97GV + H120D + Q137H | L96LG + H120N + P131S + Q137H |
| V4A + G97GV + H120D | G97GA + H120N + Q137E |
| L111V + Q137E + G211D | L111I + H120N + Q137E |
| L21LW + G100S + V139L + Q245V | L96LG + P131T + Q137H |
| V68A + Q137D | L96LG + H120N + P131S |
| L96LG + H120Q + Q137E | G97GA + H120Y + Q137H |
| K94N + H120N + P131H | G97GA + Q137D |
| G97GV + H120Q | L96LG + P131H + Q137D |

TABLE II-continued subtilase variants of the inventions having one or more of the alterations:

G97GA + Q137E + L262V
D60DG
T22TL + N62D + Q245W
T22TW + N204D + Q245I
T22TG + N62D + V139L + Q245V
G97GG + P131S + Q137H
G20* + L21F + N62D + Q245N
T22TG + N62D + V139L + Q245G
T22TL + N62D + I107V + V139L + Q245W
G97GG + H120D + Q137E
H120R + Q137D + N173S
V68A + Q245R
G97GA + H120N + S212L
G97GA + H120N + S212L
L96LG + H120D + P131H + R186L
G97GA + H120D + Q137D
S9R + A15T + A16P + G97GA +
P131S + Q137D + N204S
L21LP + T22TV + M119I + N218D + Q245I
L96LG + H120N + P131H + Q137E
L96LG + H120D + P131S + Q137E
H120N + P131T + N218D
L96LG + H120D + G160D
T22TG + N62D + V139L + Q245S
G61E + A85T + P239L + Q245C
G61E + A85T + P239L + Q245C
P131H + S144P
G97GA + Q137E
L96LG + Q137E + Y209H
G97aA + H120Q + P131H + Q137E
L111I + Q137E
G97GA + Q137E
L96LG + Q137E + Y209H
L96LG + H120N + P131S
G97GV + H120Q
L96LG + H120Q + Q137E
G97GV + P131S
K94N + H120N + P131H
N76S + L111V + P131H + Q137D
F50S + H120D + P131H
L96LG + S130*
L96LG + P131Q + Q137D
G97GA + H120D + Q137H + M222V
G97GA + H120N + Q137D + N248D
L21LW + G100S + V139L + Q245V
G20* + L21F + N62D + Q245N
L21LC + V139L + R186H + Q245M
T22TG + N62D + V139L + Q245G
T22TL + N62D + I107V + V139L + Q245W
T22TQ + S101P
T22TG + N62D + V139L + Q245V
T22TL + N62D + Q245W
T22TW + N204D + Q245I
T22TG + N62D + V139L + Q245S
L21LP + T22TY + V139L + G160D + Q245L
S130P
G61E + A85T + P239L + Q245C
L21LP + T22TV + M119I + N218D + Q245I
V68A + Q245R
T22A + V139L + Q245E
Q245F
Q245S
T260M
S9R + A15T
L21LG + T22TV + V139L + N204D + Q245N
T22G + V139L + Q245L
Q245V
N218D
A13V + I35V + N62D + Q245F
G97GA + H120D + P131H + Q137E
G97GV + Q137H
G97GV + H120N

L96LG + H120D + P131H + R186L
G97GA + R186C
V4A + G97GV + H120D

F50S + H120D + P131H
G97GA + H120N + Q137D + N248D
L96LG + P131Q + Q137D
T22G + V139L + Q245L
Q245F
Q245S
T260M
H120G + Q137E + N218D
G127E + P131R + Q137H
S130P
Q245V
N218D
T22A + V139L + Q245E
T22L + V139L + Q245V + A254S
T224A
Q245L
G61E + A85T + P239S + Q245V

G61E + A85T + Q206L + Q245R
N62NG + Q245T
G61GP + Q245L
G61E + A85T + Q137H + Y209C + Q245G
G61E + A85T + P239S + Q245C
G102S + M175T + Q245R + N252D
N62D + Q245W + N252V
N62D + Q245R + N252M
N62D + Q245W + N252S
S24P + G61E + A85T + P239S + Q245A
T22A + N62D

G61E + A85T + N218D + P239S + Q245L
S24P + G61E + A85T + P239S + Q245A
T22L + V139L + Q245V + A254S
T224A
Q245L
N62NG + Q245T
N62ND + V139L + Q245E
N62ND + V139L + N261D
G61E + A85T + Q137H + Y209C + Q245G
G61E + A85T + P239S + Q245C
N62D + Q245W + N252V
N62D + Q245R + N252M
N62D + Q245W + N252S
V68A + S99G + Q245R + N261D
G20* + L21F + N62D + Q245R
G20* + L21F + N62E + Q245R
H120D + Q137D
N77S + L96LG + H120D + P131Q
G97GA + H120N + Q137E
G97GA + Q137E + L262V
P131H + S144P
G127E + P131R + Q137H
G97GG + H120D + P131H + Q137H
G97GV + H120E + Q137H
G97GV + P131T + Q137H
G97GV + H120Q + Y263F
G97GV + S106A + P131H
G97GG + L111I + P131T + Q137H
G97GV + P131H + Q137H
G20A + G97GV + H120D + P131H
G97GA + H120D + P131S + Q137E
G97GA + Q137H
H120R + Q137D + N173S
L96LG + H120N + P131H + Q137E
L96LG + H120D + P131S + Q137E
H120N + P131T + N218D
G97GA + H120D + Q137D
G97GG + P131S + Q137H
G97GG + H120N + Q137D
H120Q + P131C + Q137D
G97GV + H120D + Q137H
A16P + G97GA + P131S +
Q137D + N204S
L96LG + H120D + G160D
G97GA + H120N + S212L
G97GA + Q137H + N218S

TABLE II-continued subtilase variants of the inventions having one or more of the alterations:

| | |
|---|---|
| G20* + L21F + *63aG + Q245R + N272V | V68A + H120N + P131S + Q137H + Q245M |
| G20* + L21F + *61aA + V68A + Q245R | V28I + V68A + Q245R + N252A |
| V68A + A194T + Q245R + N252E | V68A + Q245R + N252S |
| G20* + L21F + *62aS + N218D + Q245R | G20* + L21F + *61aS + V68A + G160D + Q245R | wherein
 (a) the variant of Table II exhibits protease activity, and
 (b) each position corresponds to a position of the amino acid sequence of subtilisin BPN', shown in FIG. 1 and SEQ ID NO: 1.

In a tenth aspect the present invention relates to a subtilase variant comprising one of the alterations N252D and N252M.

In an eleventh aspect the present invention relates to a subtilase variant comprising one or more of the alterations M119L, I, V, A, S; M175L, I, V, A, S and M222L, I, V, A, S in combination with the subtilase variants listed in tables I and II above.

Concerning alignment and numbering, reference is made to FIG. 1 which shows an alignment between subtilisin BPN' (a) (BASBPN) and subtilisin 309 (b) (BLSAVI). This alignment is in this patent application used as a reference for numbering the residues.

DEFINITIONS

Prior to discussing this invention in further detail, the following terms and conventions will first be defined.

For a detailed description of the nomenclature of amino acids and nucleic acids, we refer to WO 00/71691 beginning at page 5, hereby incorporated by reference.

Nomenclature and Conventions for Designation of Variants

In describing the various subtilase enzyme variants produced or contemplated according to the invention, the following nomenclatures and conventions have been adapted for ease of reference:

A frame of reference is first defined by aligning the isolated or parent enzyme with subtilisin BPN' (BASBPN).

The alignment can be obtained by the GAP routine of the GCG package version 9.1 to number the variants using the following parameters: gap creation penalty=8 and gap extension penalty=8 and all other parameters kept at their default values.

Another method is to use known recognized alignments between subtilases, such as the alignment indicated in WO 91/00345. In most cases the differences will not be of any importance.

Thereby a number of deletions and insertions will be defined in relation to BASBPN (SEQ ID NO: 1). In FIG. 1, subtilisin 309 (SEQ ID NO. 2) has 6 deletions in positions 36, 58, 158, 162, 163, and 164 in comparison to BASBPN. These deletions are in FIG. 1 indicated by asterixes (*).

For a detailed description of the nomenclature of modifications introduced in a polypeptide by genetic manipulation we refer to WO 00/71691 page 7-12, hereby incorporated by reference.

Proteases

Enzymes cleaving the amide linkages in protein substrates are classified as proteases, or (interchangeably) peptidases (see Walsh, 1979, *Enzymatic Reaction Mechanisms*. W.H. Freeman and Company, San Francisco, Chapter 3).

Numbering of Amino Acid Positions/Residues

If nothing else is mentioned the amino acid numbering used herein correspond to that of the subtilase BPN' (BASBPN) sequence. For further description of the BPN' sequence, see FIG. 1, SEQ ID NO: 1 or Siezen et al., *Protein Engng.* 4 (1991) 719-737.

Serine Proteases

A serine protease is an enzyme which catalyzes the hydrolysis of peptide bonds, and in which there is an essential serine residue at the active site (White, Handler and Smith, 1973 "*Principles of Biochemistry*," Fifth Edition, McGraw-Hill Book Company, NY, pp. 271-272).

The bacterial serine proteases have molecular weights in the 20,000 to 45,000 Dalton range. They are inhibited by diisopropylfluorophosphate. They hydrolyze simple terminal esters and are similar in activity to eukaryotic chymotrypsin, also a serine protease. A more narrow term, alkaline protease, covering a sub-group, reflects the high pH optimum of some of the serine proteases, from pH 9.0 to 11.0 (for review, see Priest (1977) *Bacteriological Rev.* 41 711-753).

Subtilases

A sub-group of the serine proteases tentatively designated subtilases has been proposed by Siezen et al., *Protein Engng.* 4 (1991) 719-737 and Siezen et al. *Protein Science* 6 (1997) 501-523. They are defined by homology analysis of more than 170 amino acid sequences of serine proteases previously referred to as subtilisin-like proteases. A subtilisin was previously often defined as a serine protease produced by Gram-positive bacteria or fungi, and according to Siezen et al. now is a subgroup of the subtilases. A wide variety of subtilases have been identified, and the amino acid sequence of a number of subtilases has been determined. For a more detailed description of such subtilases and their amino acid sequences reference is made to Siezen et al. (1997).

One subgroup of the subtilases, I-S1 or "true" subtilisins, comprises the "classical" subtilisins, such as subtilisin 168 (BSS168), subtilisin BPN', subtilisin Carlsberg (ALCALASE®, NOVOZYMES A/S), and subtilisin DY (BSSDY).

A further subgroup of the subtilases, I-S2 or high alkaline subtilisins, is recognized by Siezen et al. (supra). Sub-group I-S2 proteases are described as highly alkaline subtilisins and comprises enzymes such as subtilisin PB92 (BAALKP) (MAXACAL®, Genencor International Inc.), subtilisin 309 (SAVINASE®, NOVOZYMES A/S), subtilisin 147 (BLS147) (ESPERASE®, NOVOZYMES A/S), and alkaline elastase YaB (BSEYAB).

"Savinase®"

SAVINASE® is marketed by NOVOZYMES A/S. It is subtilisin 309 from *B. Lentus* and differs from BAALKP only in one position (N87S). SAVINASE® has the amino acid sequence designated b) in FIG. 1 and in SEQ ID NO: 2.

Parent Subtilase

The term "parent subtilase" describes a subtilase defined according to Siezen et al. (1991 and 1997). For further details see description of "Subtilases" above. A parent subtilase may also be a subtilase isolated from a natural source, wherein subsequent modifications have been made while retaining the characteristic of a subtilase. Furthermore, a parent subtilase may be a subtilase which has been prepared by the DNA shuffling technique, such as described by J. E. Ness et al., Nature Biotechnology, 17, 893-896 (1999).

Alternatively the term "parent subtilase" may be termed "wild type subtilase".

For reference a table of the acronyms for various subtilases mentioned herein is provided, for further acronyms, see Siezen et al., *Protein Engng.* 4 (1991) 719-737 and Siezen et al. *Protein Science* 6 (1997) 501-523.

TABLE III

| Organism | enzyme | acronym |
|---|---|---|
| Bacteria: Gram-positive | | |
| *Bacillus subtilis* 168 | subtilisin I168, apr | BSS168 |
| *Bacillus amyloliquefaciens* | subtilisin BPN' (NOVO) | BASBPN |
| *Bacillus subtilis* DY | subtilisin DY | BSSDY |
| *Bacillus licheniformis* | subtilisin Carlsberg | BLSCAR |
| *Bacillus lentus* | subtilisin 309 | BLSAVI |
| *Bacillus lentus* | subtilisin 147 | BLS147 |
| *Bacillus alcalophilus* PB92 | subtilisin PB92 | BAPB92 |
| Bacillus YaB | alkaline elastase YaB | BYSYAB |
| *Thermoactinomyces vulgaris* | thermitase | TVTHER |

Modification(s) of a Subtilase Variant

The term "modification(s)" used herein is defined to include chemical modification of a subtilase as well as genetic manipulation of the DNA encoding a subtilase. The modification(s) can be replacement(s) of the amino acid side chain(s), substitution(s), deletion(s) and/or insertions in or at the amino acid(s) of interest.

Subtilase Variants

In the context of this invention, the term subtilase variant or mutated subtilase means a subtilase that has been produced by an organism which is expressing a mutant gene derived from a parent microorganism which possessed an original or parent gene and which produced a corresponding parent enzyme, the parent gene having been mutated in order to produce the mutant gene from which said mutated subtilase protease is produced when expressed in a suitable host.

Homologous Subtilase Sequences

The homology between two amino acid sequences is in this context described by the parameter "identity".

In order to determine the degree of identity between two subtilases the GAP routine of the GCG package version 9.1 can be applied (infra) using the same settings. The output from the routine is besides the amino acid alignment the calculation of the "Percent Identity" between the two sequences.

Based on this description it is routine for a person skilled in the art to identify suitable homologous subtilases, which can be modified according to the invention.

Isolated Polynucleotides

The term "isolated", when applied to a polynucleotide, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, Nature 316:774-78, 1985). The term "an isolated polynucleotide" may alternatively be termed "a cloned polynucleotide".

Isolated Proteins

When applied to a protein, the term "isolated" indicates that the protein has been removed from its native environment. In a preferred form, the isolated protein is substantially free of other proteins, particularly other homologous proteins (i.e. "homologous impurities" (see below)).

An isolated protein is more than 10% pure, preferably more than 20% pure, more preferably more than 30% pure, as determined by SDS-PAGE. Further it is preferred to provide the protein in a highly purified form, i.e., more than 40% pure, more than 60% pure, more than 80% pure, more preferably more than 95% pure, and most preferably more than 99% pure, as determined by SDS-PAGE.

The term "isolated protein" may alternatively be termed "purified protein".

Homologous Impurities

The term "homologous impurities" means any impurity (e.g. another polypeptide than the subtilase of the invention), which originate from the homologous cell where the subtilase of the invention is originally obtained from.

Obtained from

The term "obtained from" as used herein in connection with a specific microbial source, means that the polynucleotide and/or subtilase produced by the specific source, or by a cell in which a gene from the source has been inserted.

Substrate

The term "substrate" used in connection with a substrate for a protease should be interpreted in its broadest form as comprising a compound containing at least one peptide (amide) bond susceptible to hydrolysis by a subtilisin protease.

Product

The term "product" used in connection with a product derived from a protease enzymatic reaction should, in the context of the present invention, be interpreted to include the products of a hydrolysis reaction involving a subtilase protease. A product may be the substrate in a subsequent hydrolysis reaction.

Wash Performance

In the present context the term "wash performance" is used as an enzyme's ability to remove proteinaceous or organic stains present on the object to be cleaned during e.g. wash or hard surface cleaning. See also the wash performance test in Example 3 herein.

19

BRIEF DESCRIPTION OF THE DRAWING

FIG. 1 shows an alignment between subtilisin BPN' (a) and Savinase® (b) using the GAP routine mentioned above.

DETAILED DESCRIPTION OF THE INVENTION

The present invention relates to novel subtilase variants exhibiting alterations relative to the parent subtilase in one or more properties including: Wash performance, thermal stability, storage stability or catalytic activity.

Variants which are contemplated as being part of the invention are such variants where, when compared to the wild-type subtilase, one or more amino acid residues has been substituted, deleted or inserted, said variants comprising at least
a) an insertion, substitution or deletion of one of the amino acid residues K, H, R, E, D, Q, N, C, V, L, I, P, M, F, W, Y, G, A, S, T in one or more of the positions 62, 68, 97, 98, 99, 106, 131, 170, 245, 252, in combination with at least one of the following modifications

*0AQSVPWG; A1T,V; Q2L; S3T,A,L; V4L,A; I8V,T; S9G,D,R,K,L,V; R10H,K; V11A; Q12D; A13V; P14S,T,D,A,M,V,K,Q,L,H,R,I; A15M,T; A16P; H17R; N18S,H; R19W,K,L,F,G,I; G20*,R,A; L21F,LP,LW,LA,LG; T22S,A,K,TV,TG,TL,TW,TV,G,L,TY; G23S; S24P; K27R,V28I; V30I; I35T,V; T38S; P40L; N43D; R45H,K; G46D; A48T; S49N; F50S; V51A,I,D; P52V,A; P55S,A; S57P; G61E,D,S,R,GP; N62D,ND,NE,DE,NG,E,S; V68A,S,L,I; T71A; I72V; L75I; N76S,D; N77S; S78T; V81A; A85T; S87C; A88V,T; E89G; K94N; V95C,T; L96LA,LG; G97E,D,W,A,GG,GA,GV,N,GS; A98S,D,E,T,AS,AD,AV,AE,AH,Q,N,M,L,G,R,V,S; S99D,L,A,AD,SD,SM,SG,DA,P,G,N,C,M,V,I; G100S,GE,C; S101SA, SK; G102D,S; S103D,E,Y,L,Q,H,T; V104T,S,R,I,N,M,L,D; S106D,E,T,M,G,A,L,F,I; I107T,V,M; A108V,T,S; L111I,V; A114V; N116S,D; G118D; M119L,I,V,A,S; H120N,D,Q,K,E,Y,S; V121A; L124C; L126I; G127E; S128N,I,G,C; P129PSN,T,E,D,S,N,A; S130P,T,C,*; P131M,F,W,L,A,H,T,*,PA,S,Q,R,E,G,D,C; S132G,T; A133ASA; T134A; Q137H,E,D; A138G,V; V139L,I; N140D, K; T143A; S144D, N,P; R145G; V150I; A151V,G; A152P; A158T,V,C,E,L,D, M; G160A,D; S163G,C,N,A; Y167K,A, I; A168G; A169G; R170C,S,H,L; Y171C; A172V; N173D; A174V; M175L,I,V,A,S,T; N183D; N184D,S; N185S,D; R186L,C,H; S188G; S190A; Y192H; G195F,E; V203S,A,L,Q,M, F,I; N204T,D,S; Q206L; Y209C,H; G211D; S212N,L; T213A; Y214C,H; A215D,T; N218D,S; M222L,I,V,A,S; A223G; T224A,S; A228T; A230V; A232S,L,T,P; V234I; Q236A,L,D,T,C,M,F,S; K237R; N238D; P239T,S; S240F; S242T; V244I,M,A; Q245R,K,E,D,T,F,N,V,W,G,I,S,C,L,A, M; N248P,D,S; K251E,R; N252G,H,D,V,M,S,T,E,Y,S,Q,K, A,L; A254S; T255A,S; S256N,R,G; L257G; G258K, S259A, N,G; T260A,R; N261D; L262S, Q,V; Y263H,F; G264E; S265G,R,N; V268L,I; N269T; N296K; E271A; T274S,L, A,R or
b) one of the following combination variants A108T+ L111V; L124I+S125A; P129S+S130AT; L96LA+ A151G+V203A; S49N+V203L+N218D; S3T+A16P+ R45C+G100S+A230V; I8V+R19K+V139I; N76D+ A174AL+A194P+A230V; N185R; N62NE; H120Q+ Q137E, G61GE, G61GS, G100L, A133D, V68A, N123D, L111F+Y263H, V11A+G61GE+V227A+ S240F, A133E+S144K+N218D, S128A+P129S+ S130SP, S9R+A15T+T22TQ+S101P, S9R+A15T+ H120R+Q137D+N173S, G97E, Q245W, S9R+A15T+ L96LG+Q137E+Y209H, S9R+A15T+L111V+

20

Q137E+G211D, S9R+A15T+L111I+Q137E, S9R+ A15T+L111I+H120N+Q137E, S9R+A15T+L96LG+ H120Q+Q137E, S9R+A15T+T260M, S9R+A15T, Q245I, S9R+A15T+H120G+Q137E+N218D, S9R+ A15T+S130P, Q245F, S9R+A15T+N218D, G63E+ N76D+A194P+A230V, S9R+A15T+T224A, G100S, S9R+A15T+D60DG, A138V+V139I+A194P+ N218D+A230V, A108V+A169G+R170A+Y171H, I8V+P14L+R19L+V30I+I35V+S57P+P129S+ Q137D+S144D+S256N, A133D+T134S+Q137A, Q137D, A98AH, V51D, Q12E+P14L+A15T, G63E+ N76D+A194P+A230V, Q12E+P14L+A15T, G97GS or
c) one or more modifications in position 68, wherein said modification(s) comprise(s): deletion, insertion and/or substitution of an amino acid residue selected from the group consisting of K, H, R, E, D, Q, N, C, V, L, I, P, M, F, W, Y, G, A, S and T.

Further, variants of the present invention comprises at least one or more of the alterations indicated in Table I and II, wherein
(a) the variants of Table I and II has protease activity, and
(b) each position corresponds to a position of the amino acid sequence of subtilisin BPN' (SEQ ID NO: 1).

A subtilase variant of the first aspect of the invention may be a parent or wild-type subtilase identified and isolated from nature. Such a parent wild-type subtilase may be specifically screened for by standard techniques known in the art.

One preferred way of doing this may be by specifically PCR amplify conserved DNA regions of interest from subtilases from numerous different microorganism, preferably different *Bacillus* strains.

Subtilases are a group of conserved enzymes, in the sense that their DNA and amino acid sequences are homologous. Accordingly it is possible to construct relatively specific primers flanking the polynucleotide sequences of interest.

Using such PCR primers to amplify DNA from a number of different microorganisms, preferably different *Bacillus* strains, followed by DNA sequencing of said amplified PCR fragments, it will be possible to identify strains which produce subtilase variants of the invention. Having identified the strain and a partial DNA sequence of such a subtilase of interest, it is routine work for a person skilled in the art to complete cloning, expression and purification of such a subtilase. However, it is envisaged that a subtilase variant of the invention is predominantly a variant of a parent subtilase.

A subtilase variant suitable for the uses described herein may be constructed by standard techniques known in the art such as by site-directed/random mutagenesis or by DNA shuffling of different subtilase sequences. See the "Material and Methods" section and Example 1 herein (vide infra) for further details.

As will be acknowledged by the skilled person, the variants described herein may comprise one or more further modifications, in particular one or more further substitutions or insertions. Moreover, the variants described herein may encompass mutation at more than just one position. For example the variant according to the invention may contain mutations at one position, two positions, three positions or more than three positions, such as four to eight positions.

It is preferred that the parent subtilase belongs to the subgroups I-S1 or I-S2, especially subgroup I-S2, both for enzymes from nature or from the artificial creation of diversity, and for designing and producing variants from a parent subtilase.

In relation to variants from subgroup I-S1, it is preferred to select a parent subtilase from the group consisting of BSS168 (BSSAS, BSAPRJ, BSAPRN, BMSAMP), BASBPN, BSSDY, BLSCAR (BLKERA, BLSCA1, BLSCA2, BLSCA3), BSSPRC, and BSSPRD, or functional variants thereof having retained the characteristic of sub-group I-S1.

In relation to variants from subgroup I-S2 it is preferred to select a parent subtilase from the group consisting of BSAPRQ, BLS147 (BSAPRM, BAH101), BLSAVI (BSKSMK, BAALKP, BLSUBL), BYSYAB, BAPB92, TVTHER, and BSAPRS, or functional variants thereof having retained the characteristic of sub-group I-S2.

In particular, the parent subtilase is BLSAVI (Savinase®, NOVOZYMES A/S), and a preferred subtilase variant of the invention is accordingly a variant of Savinase®.

The present invention also encompasses any of the above mentioned subtilase variants in combination with any other modification to the amino acid sequence thereof. Especially combinations with other modifications known in the art to provide improved properties to the enzyme are envisaged. The art describes a number of subtilase variants with different improved properties and a number of those are mentioned in the "Background of the invention" section herein (vide supra). Those references are disclosed here as references to identify a subtilase variant, which advantageously can be combined with a subtilase variant described herein.

Such combinations comprise the positions: 222 (improves oxidation stability), 218 (improves thermal stability), substitutions in the $Ca^{2+}$-binding sites stabilizing the enzyme, e.g. position 76, and many other apparent from the prior art.

In further embodiments a subtilase variant described herein may advantageously be combined with one or more modification(s) in any of the positions:

27, 36, 56, 76, 87, 95, 96, 97, 98, 99, 100, 101, 102, 103, 104, 120, 123, 159, 167, 170, 206, 218, 222, 224, 232, 235, 236, 245, 248, 252 and 274.

Specifically, the following BLSAVI, BLSUBL, BSKSMK, and BAALKP modifications are considered appropriate for combination:

K27R, *36D, S56P, N62D, V68A, N76D, S87N, G97N, S99SE, S101G, S103A, V104A, V104I, V104N, V104Y, S106A, H120D, H120N, N123S, G159D, Y167A, R170S, R170L, A194P, N204D, V205I, Q206E, L217D, N218S, N218D, M222S, M222A, T224S, A232V, K235L, Q236H, Q245R, N248D, N252K and T274A.

Furthermore variants comprising any of the modifications K27R+V104Y+N123S+T274A, N76D+S103A+V104I, N76D+V104A, S87N+S101G+V104N, S99D+S101R+S103A+V104I+G160S, S3T+V4I+S99D+S101R+S103A+V104I+G160S+A194P+V199M+V205I+L217D, S3T+V4I+S99D+S101R+S103A+V104I+G160S+V199M+V205I+L217D, S3T+V4I+S99D+S101R+S103A+V104I+G160S+V205I, S101G+V104N, or other combinations of the modifications K27R, *36D, S56P, N62D, V68A, N76D, S87N, G97N, S99SE, S101G, S103A, V104A, V104I, V104N, V104Y, S106A, H120D, H120N, N123S, G159D, Y167A, R170S, R170L, A194P, N204D, V205I, Q206E, L217D, N218S, N218D, M222A, M222S, T224S, A232V, K235L, Q236H, Q245R, N248D, N252K and T274A in combination with any one or more of the modification(s) mentioned above exhibit improved properties.

A particular interesting variant is a variant, which, in addition to modifications according to the invention, contains the following substitutions:

S101G+S103A+V104I+G159D+A232V+Q236H+Q245R+N248D+N252K.

Moreover, subtilase variants of the main aspect(s) of the invention are preferably combined with one or more modification(s) in any of the positions 129, 131 and 194, preferably as 129K, 131H and 194P modifications, and most preferably as P129K, P131H and A194P modifications. Any of those modification(s) are expected to provide a higher expression level of the subtilase variant in the production thereof.

The wash performance of a selected variant of the invention may be tested in the wash performance test disclosed in Example 3 herein. The wash performance test may be employed to assess the ability of a variant, when incorporated in a standard or commercial detergent composition, to remove proteinaceous stains from a standard textile as compared to a reference system, namely the parent subtilase or a similar subtilase exhibiting an even better wash performance (incorporated in the same detergent system and tested under identical conditions). The enzyme variants of the present application were tested using the Automatic Mechanical Stress Assay (AMSA). With the AMSA test the wash performance of a large quantity of small volume enzyme-detergent solutions can be examined rapidly. Using this test, the wash performance of a selected variant can be initially investigated, the rationale being that if a selected variant does not show a significant improvement in the test compared to the parent subtilase, it is normally not necessary to carry out further test experiments.

Therefore, variants which are particularly interesting for the purposes described herein, are such variants which, when tested in a commercial detergent composition such as a US type detergent, an Asian type, a European type or a Latin American type detergent as described in the wash performance test (Example 3), shows an improved wash performance as compared to the parent subtilase tested under identical conditions.

The improvement in the wash performance may be quantified by calculating the so-called intensity value (Int) defined in Example 3, herein.

In a very interesting embodiment of the invention, the variant of the invention, when tested in the wash performance test has a Performance Score (S) of at least 1, preferably a Performance Score of 2, where:

S (2)=variant performs better than the reference at all three enzyme concentrations (5, 10 and 30 nM), S (1)=variant performs better than the reference at one or two concentrations.

Evidently, it is preferred that the variant of the invention fulfils the above criteria on at least the stated lowest level, more preferably at the stated highest level.

Producing a Subtilase Variant

Many methods for cloning a subtilase and for introducing substitutions, deletions or insertions into genes (e.g. subtilase genes) are well known in the art.

In general standard procedures for cloning of genes and introducing mutations (random and/or site directed) into said genes may be used in order to obtain a subtilase variant of the invention. For further description of suitable techniques reference is made to Example 1 herein (vide infra) and (Sambrook et al. (1989) Molecular cloning: A laboratory manual, Cold Spring Harbor lab., Cold Spring Harbor, N.Y.; Ausubel, F. M. et al. (eds.) "Current protocols in Molecular Biology". John Wiley and Sons, 1995; Harwood, C. R., and Cutting, S. M. (eds.) "Molecular Biological Methods for *Bacillus*". John Wiley and Sons, 1990), and WO 96/34946.

Further, a subtilase variant may be constructed by standard techniques for artificial creation of diversity, such as by DNA shuffling of different subtilase genes (WO 95/22625; Stemmer WPC, Nature 370:389-91 (1994)). DNA shuffling of e.g. the gene encoding Savinase® with one or more partial subtilase sequences identified in nature, will after subsequent screening for improved wash performance variants, provide subtilase variants suitable for the purposes described herein.

Expression Vectors

A recombinant expression vector comprising a DNA construct encoding the enzyme of the invention may be any vector that may conveniently be subjected to recombinant DNA procedures.

The choice of vector will often depend on the host cell into which it is to be introduced. Thus, the vector may be an autonomously replicating vector, i.e. a vector that exists as an extra-chromosomal entity, the replication of which is independent of chromosomal replication, e.g. a plasmid.

Alternatively, the vector may be one that on introduction into a host cell is integrated into the host cell genome in part or in its entirety and replicated together with the chromosome(s) into which it has been integrated.

The vector is preferably an expression vector in which the DNA sequence encoding the enzyme of the invention is operably linked to additional segments required for transcription of the DNA. In general, the expression vector is derived from plasmid or viral DNA, or may contain elements of both. The term, "operably linked" indicates that the segments are arranged so that they function in concert for their intended purposes, e.g. transcription initiates in a promoter and proceeds through the DNA sequence coding for the enzyme.

The promoter may be any DNA sequence that shows transcriptional activity in the host cell of choice and may be derived from genes encoding proteins either homologous or heterologous to the host cell.

Examples of suitable promoters for use in bacterial host cells include the promoter of the *Bacillus stearothermophilus* maltogenic amylase gene, the *Bacillus licheniformis* alpha-amylase gene, the *Bacillus amyloliquefaciens* alpha-amylase gene, the *Bacillus subtilis* alkaline protease gene, or the *Bacillus pumilus* xylosidase gene, or the phage Lambda $P_R$ or $P_L$ promoters or the *E. coli* lac, trp or tac promoters.

The DNA sequence encoding the enzyme of the invention may also, if necessary, be operably connected to a suitable terminator.

The recombinant vector of the invention may further comprise a DNA sequence enabling the vector to replicate in the host cell in question. The vector may also comprise a selectable marker, e.g. a gene the product of which complements a defect in the host cell, or a gene encoding resistance to e.g. antibiotics like kanamycin, chloramphenicol, erythromycin, tetracycline, spectinomycine, or the like, or resistance to heavy metals or herbicides.

To direct an enzyme of the present invention into the secretory pathway of the host cells, a secretory signal sequence (also known as a leader sequence, prepro sequence or pre sequence) may be provided in the recombinant vector. The secretory signal sequence is joined to the DNA sequence encoding the enzyme in the correct reading frame. Secretory signal sequences are commonly positioned 5' to the DNA sequence encoding the enzyme. The secretory signal sequence may be that normally associated with the enzyme or may be from a gene encoding another secreted protein.

The procedures used to ligate the DNA sequences coding for the present enzyme, the promoter and optionally the terminator and/or secretory signal sequence, respectively, or to assemble these sequences by suitable PCR amplification schemes, and to insert them into suitable vectors containing the information necessary for replication or integration, are well known to persons skilled in the art (cf., for instance, Sambrook et al., op.cit.).

Host Cells

The DNA sequence encoding the present enzyme introduced into the host cell may be either homologous or heterologous to the host in question. If homologous to the host cell, i.e. produced by the host cell in nature, it will typically be operably connected to another promoter sequence or, if applicable, another secretory signal sequence and/or terminator sequence than in its natural environment. The term "homologous" is intended to include a DNA sequence encoding an enzyme native to the host organism in question. The term "heterologous" is intended to include a DNA sequence not expressed by the host cell in nature. Thus, the DNA sequence may be from another organism, or it may be a synthetic sequence.

The host cell into which the DNA construct or the recombinant vector of the invention is introduced may be any cell that is capable of producing the present enzyme and includes bacteria, yeast, fungi and higher eukaryotic cells including plants.

Examples of bacterial host cells which, on cultivation, are capable of producing the enzyme of the invention are gram-positive bacteria such as strains of *Bacillus*, such as strains of *B. alkalophilus, B. amyloliquefaciens, B. brevis, B. circulans, B. coagulans, B. lautus, B. lentus, B. licheniformis, B. megaterium, B. stearothermophilus, B. subtilis*, or *B. thuringiensis*, or strains of *Streptomyces*, such as *S. lividans* or *S. murinus*, or gram-negative bacteria such as *Escherichia coli*.

The transformation of the bacteria may be effected by protoplast transformation, electroporation, conjugation, or by using competent cells in a manner known per se (cf. Sambrook et al., supra).

When expressing the enzyme in bacteria such as *E. coli*, the enzyme may be retained in the cytoplasm, typically as insoluble granules (known as inclusion bodies), or may be directed to the periplasmic space by a bacterial secretion sequence. In the former case, the cells are lysed and the granules are recovered and denatured after which the enzyme is refolded by diluting the denaturing agent. In the latter case, the enzyme may be recovered from the periplasmic space by disrupting the cells, e.g. by sonication or osmotic shock, to release the contents of the periplasmic space and recovering the enzyme.

When expressing the enzyme in gram-positive bacteria such as *Bacillus* or *Streptomyces* strains, the enzyme may be retained in the cytoplasm, or may be directed to the extracellular medium by a bacterial secretion sequence. In the latter case, the enzyme may be recovered from the medium as described below.

Methods for Producing a Subtilase Variant

The present invention provides a method of producing an isolated enzyme according to the invention, wherein a suitable host cell, which has been transformed with a DNA sequence encoding the enzyme, is cultured under conditions permitting the production of the enzyme, and the resulting enzyme is recovered from the culture.

When an expression vector comprising a DNA sequence encoding the enzyme is transformed into a heterologous host cell it is possible to enable heterologous recombinant production of the enzyme of the invention. Thereby it is possible to make a highly purified subtilase composition, characterized in being free from homologous impurities.

The medium used to culture the transformed host cells may be any conventional medium suitable for growing the host cells in question. The expressed subtilase may conveniently be secreted into the culture medium and may be recovered there-from by well-known procedures including separating the cells from the medium by centrifugation or filtration, precipitating proteinaceous components of the medium by means of a salt such as ammonium sulfate, followed by chromatographic procedures such as ion exchange chromatography, affinity chromatography, or the like.

Cleaning and Detergent Compositions

The enzyme of the invention may be added to and thus become a component of a detergent composition. In general, cleaning and detergent compositions are well described in the art and reference is made to WO 96/34946; WO 97/07202; WO 95/30011 for further description of suitable cleaning and detergent compositions.

The detergent composition of the invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the invention provides a detergent additive comprising the enzyme of the invention. The detergent additive as well as the detergent composition may comprise one or more other enzymes such as a protease, a lipase, a cutinase, an amylase, a carbohydrase, a cellulase, a pectinase, a mannanase, an arabinase, a galactanase, a xylanase, an oxidase, e.g., a laccase, and/or a peroxidase.

In general the properties of the chosen enzyme(s) should be compatible with the selected detergent, (i.e. pH-optimum, compatibility with other enzymatic and non-enzymatic ingredients, etc.), and the enzyme(s) should be present in effective amounts.

Proteases: Suitable proteases include those of animal, vegetable or microbial origin. Microbial origin is preferred. Chemically modified or protein engineered mutants are included. The protease may be a serine protease or a metallo protease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like proteases are trypsin (e.g. of porcine or bovine origin) and the *Fusarium* protease described in WO 89/06270 and WO 94/25583.

Examples of useful proteases are the variants described in WO 92/19729, WO 98/20115, WO. 98/20116, and WO 98/34946, especially the variants with substitutions in one or more of the following positions: 27, 36, 57, 76, 87, 97, 101, 104, 120, 123, 167, 170, 194, 206, 218, 222, 224, 235 and 274.

Preferred commercially available protease enzymes include Durazym®, Relase®, Alcalase®, Savinase®, Primase®, Duralase®, Esperase®, Ovozyme® and Kannas® (Novozymes A/S), Maxatase™, Maxacal™, Maxapem™, Properase™, Purafect™, Purafect OxP™, FN2™, FN3™ and FN4™ (Genencor International, Inc.).

Lipases: Suitable lipases include those of bacterial or fungal origin. Chemically modified or protein engineered mutants are included. Examples of useful lipases include lipases from *Humicola* (synonym *Thermomyces*), e.g. from *H. lanuginosa* (*T. lanuginosus*) as described in EP 258 068 and EP 305 216 or from *H. insolens* as described in WO 96/13580, a *Pseudomonas* lipase, e.g. from *P. alcaligenes* or *P. pseudoalcaligenes* (EP 218 272), *P. cepacia* (EP 331 376), *P. stutzeri* (GB 1,372,034), *P. fluorescens*, *Pseudomonas* sp. strain SD 705 (WO 95/06720 and WO 96/27002), *P. wisconsinensis* (WO 96/12012), a *Bacillus* lipase, e.g. from *B. subtilis* (Dartois et al. (1993), Biochemica et Biophysica Acta, 1131, 253-360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipase enzymes include Lipex®, Lipolase® and Lipolase Ultra® (Novozymes A/S).

Amylases: Suitable amylases ($\alpha$ and/or $\beta$) include those of bacterial or fungal origin. Chemically modified or protein engineered mutants are included. Amylases include, for example, $\alpha$-amylases obtained from *Bacillus*, e.g. a special strain of *B. licheniformis*, described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Commercially available amylases are Duramyl®, Termamyl®, Fungamyl® and BAN® (Novozymes A/S), Rapidase™ and Purastar™ (from Genencor International Inc.).

Cellulases: Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g. the fungal cellulases produced from *Humicola insolens, Myceliophthora thermophila* and *Fusadum oxysporum* disclosed in U.S. Pat. No. 4,435,307, U.S. Pat. No. 5,648,263, U.S. Pat. No. 5,691,178, U.S. Pat. No. 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. No. 5,457,046, U.S. Pat. No. 5,686,593, U.S. Pat. No. 5,763,254, WO 95/24471, WO 98/12307 and PCT/DK98/00299.

Commercially available cellulases include Celluzyme®, and Carezyme® (Novozymes A/S), Clazinase™, and Puradax HA™ (Genencor International Inc.), and KAC-500 (B)™ (Kao Corporation).

Peroxidases/Oxidases: Suitable peroxidases/oxidases include those of plant, bacterial or fungal origin. Chemically modified or protein engineered mutants are included. Examples of useful peroxidases include peroxidases from *Coprinus*, e.g. from *C. cinereus*, and variants thereof as those described in WO 93/24618, WO 95/10602, and WO 98/15257. Commercially available peroxidases include Guardzyme® (Novozymes A/S).

The detergent enzyme(s) may be included in a detergent composition by adding separate additives containing one or more enzymes, or by adding a combined additive comprising all of these enzymes. A detergent additive of the invention, i.e. a separate additive or a combined additive, can be formulated e.g. as a granulate, a liquid, a slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition of the invention may be in any convenient form, e.g., a bar, a tablet, a powder, a granule, a paste or a liquid. A liquid detergent may be aqueous, typically containing up to 70% water and 0-30% organic solvent, or non-aqueous.

The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0-65% of a detergent builder or complexing agent such as zeolite, diphosphate, triphosphate, phosphonate, carbonate, citrate, nitrilotriacetic acid, ethylene-diaminetetraacetic acid, diethylenetriaminepentaacetic acid, alkyl- or alkenyl-succinic acid, soluble silicates or layered silicates (e.g. SKS-6 from Hoechst).

The detergent may comprise one or more polymers. Examples are carboxymethyl-cellulose, poly(vinylpyrrolidone), poly(ethylene glycol), poly(vinyl alcohol), poly(vinyl-pyridine-N-oxide), poly(vinylimidazole), polycarboxylates such as poly-acrylates, maleic/acrylic acid copolymers and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine or nonanoyloxybenzenesulfonate. Alternatively, the bleaching system may comprise peroxyacids of e.g. the amide, imide, or sulfone type.

The detergent may also contain other conventional detergent ingredients such as e.g. fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

Variations in local and regional conditions, such as water hardness and wash temperature calls for regional detergent compositions. Detergent Examples 1 and 2 provide ranges for the composition of a typical Latin American detergent and a typical European powder detergent respectively.

Detergent Example 1

Typical Latin-American Detergent Composition

| Group | Subname | Content |
| --- | --- | --- |
| Surfactants | | 0-30% |
| | Sulphonates | 0-30% |
| | Sulphates | 0-5% |
| | Soaps | 0-5% |
| | Non-ionics | 0-5% |
| | Cationics | 0-5% |
| | FAGA | 0-5% |
| Bleach | | 0-20% |
| | SPT/SPM | 0-15% |
| | NOBS, TAED | 0-5% |
| Builders | | 0-60% |
| | Phosphates | 0-30% |
| | Zeolite | 0-5% |
| | Na2OSiO2 | 0-10% |
| | Na2CO3 | 0-20% |
| Fillers | | 0-40% |
| | Na2SO4 | 0-40% |
| Others | | up to 100% |
| | Polymers | |
| | Enzymes | |
| | Foam regulators | |
| | Water | |
| | Hydrotropes | |
| | Others | |

Detergent Example 2

Typical European Powder Detergent Composition

| Group | Subname | Content |
| --- | --- | --- |
| Surfactants | | 0-30% |
| | Sulphonates | 0-20% |
| | Sulphates | 0-15% |
| | Soaps | 0-10% |
| | Non-ionics | 0-10% |
| | Cationics | 0-10% |
| | Other | 0-10% |
| Bleach | | 0-30% |
| | SPT/SPM | 0-30% |
| | NOBS + TAED | 0-10% |
| Builders | | 0-60% |
| | Phosphates | 0-40% |
| | Zeolite | 0-40% |
| | Na2OSiO2 | 0-20% |
| | Na2CO3 | 0-20% |
| Fillers | | 0-40% |
| | Na2SO4 | 0-40% |
| | NaCl | 0-40% |
| Others | | up to 100% |
| | Polymers | |
| | Enzymes | |
| | Foam regulators | |
| | Water | |
| | Hydrotropes | |
| | Others | |

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in e.g. WO 92/19709 and WO 92/19708.

It is at present contemplated that in the detergent compositions any single enzyme, in particular the enzyme of the invention, may be added in an amount corresponding to 0.01-200 mg of enzyme protein per liter of wash liquor, preferably 0.05-50 mg of enzyme protein per liter of wash liquor, in particular 0.1-10 mg of enzyme protein per liter of wash liquor.

The enzyme of the invention may additionally be incorporated in the detergent formulations disclosed in WO 97/07202 which is hereby incorporated as reference.

Materials and Methods

Textiles:

Standard textile pieces are obtained from EMPA St. Gallen, Lerchfeldstrasse 5, CH-9014 St. Gallen, Switzerland. Especially type EMPA116 (cotton textile stained with blood, milk and ink) and EMPA117 (polyester/cotton textile stained with blood, milk and ink).

Strains and Plasmids:

Bacillus lentus strain 309 is deposited with the NCIB and accorded the accession number NCIB 10309, and described in U.S. Pat. No. 3,723,250 incorporated by reference herein. The parent subtilase 309 or Savinase® can be obtained from Strain 309. The expression host organism is Bacillus subtilis.

The plasmid pSX222 is used as E. coli—B. subtilis shuffle vector and B. subtilis expression vector (as described in WO 96/34946).

General Molecular Biology Methods:

Unless otherwise mentioned the DNA manipulations and transformations are performed using standard methods of molecular biology (Sambrook et al. (1989) Molecular cloning: A laboratory manual, Cold Spring Harbor lab., Cold Spring Harbor, N.Y.; Ausubel, F. M. et al. (eds.) "Current protocols in Molecular Biology". John Wiley and Sons, 1995; Harwood, C. R., and Cutting, S. M. (eds.) "Molecular Biological Methods for Bacillus". John Wiley and Sons, 1990).

Enzymes for DNA Manipulations

Unless otherwise mentioned all enzymes for DNA manipulations, such as e.g. restriction endonucleases, ligases etc., are obtained from New England Biolabs, Inc. Enzymes for DNA manipulations are used according to the specifications of the suppliers.

Fermentation:

Fermentations for the production of subtilase enzymes are performed at pH 7.3 and 37° C. on a rotary shaking table at 225 rpm. in 50 ml tubes containing 15 ml double TY media for 2-3 days.

For a description of TY media, see page 1.1.3, Media Preparation and Bacteriological Tools in "Current protocols in Molecular Biology". John Wiley and Sons, 1995; Harwood, C. R., and Cutting, S. M. (eds.).

Purification

The subtilase variant secreted from the host cells may conveniently be recovered from the culture medium by well-known procedures, including separating the cells from the medium by centrifugation or filtration, and precipitating proteinaceous components of the medium by means of a salt such as ammonium sulfate, followed by the use of chromatographic procedures such as ion exchange chromatography, affinity chromatography, or the like.

Wash Performance Test

In order to assess the wash performance of selected subtilase variants in detergent compositions, washing experiments are performed. The enzyme variants are tested using the Automatic Mechanical Stress Assay (AMSA). With the AMSA test the wash performance of a large quantity of small volume enzyme-detergent solutions can be examined. The AMSA plate has a number of slots for test solutions and a lid firmly squeezing the textile swatch to be washed against all the slot openings. During the washing time, the plate, test solutions, textile and lid are vigorously shaken to bring the test solution in contact with the textile and apply mechanical stress. For further description see WO 02/42740 especially the paragraph "Special method embodiments" at page 23-24.

Detergents

Detergents for wash performance tests of the subtilase enzymes of the invention can be obtained by purchasing fully formulated commercial detergents at the market and subsequently inactivate the enzymatic components by heat treatment (5 minutes at 85° C. in aqueous solution). Moreover a commercial detergent base without enzymes can be purchased directly from the manufacturer. Further a suitable model detergent can be composed according to the provisions at page 19-24 herein and used for wash performance tests.

Example 1

Construction and Expression of Enzyme Variants

Site-Directed Mutagenesis:

Subtilisin 309 (Savinase®) site-directed variants of the invention comprising specific insertions/deletions/substitutions are made by traditional cloning of DNA fragments (Sambrook et al., Molecular Cloning: A Laboratory Manual, 2nd Ed., Cold Spring Harbor, 1989) produced by PCR with oligos containing the desired mutations.

The template plasmid DNA may be pSX222, or an analogue of this containing a variant of subtilisin 309. Mutations are introduced by oligo directed mutagenesis to the construction of variants.

The subtilisin 309 variants are transformed into E. coli. DNA purified from an over night culture of these transformants is transformed into B. subtilis by restriction endonuclease digestion, purification of DNA fragments, ligation, transformation of B. subtilis. Transformation of B. subtilis is performed as described by Dubnau et al., 1971, J. Mol. Biol. 56, pp. 209-221.

Site-Directed Mutagenesis in Order to Introduce Mutations in a Specific Region:

The overall strategy used to perform site-directed mutagenesis is:

Mutagenic primers (oligonucleotides) are synthesized corresponding to the DNA sequence flanking the sites of mutation, separated by the DNA base pairs defining the insertions/deletions/substitutions.

Subsequently, the resulting mutagenic primers are used in a PCR reaction with the modified plasmid pSX222. The resulting PCR fragment is purified and extended in a second PCR-reaction, the resulting PCR product is purified and extended in a third PCR-reaction before being digested by endonucleases and cloned into the E. coli—B. subtilis shuttle vector pSX222. The PCR reactions are performed under normal conditions. The plasmid DNA is transformed into E. coli by well-known techniques and one E. coli colony is sequenced to confirm the mutation designed.

Each of the variants listed in Table I at page 2 herein can be constructed as described above.

In order to purify subtilase variants of the invention, the pSX222 expression plasmid comprising a variant of the invention was transformed into a competent *B. subtilis* strain and fermented as described above.

Example 2

Purification and Assessment of Enzyme Concentration

After fermentation purification of subtilisin variants is accomplished using Hydrophobic Charge Induction Chromatography (HCIC) and subsequent vacuum filtration.

To capture the enzyme, the HCIC uses a cellulose matrix to which 4-Mercapto-Ethyl-Pyridine (4-MEP) is bound.

Beads of the cellulose matrix sized 80-100 μm are mixed with a media containing yeast extract and the transformed *B. subtilis* capable of secreting the subtilisin variants and incubated at pH 9.5 in Unifilter® microplates.

As 4-MEP is hydrophobic at pH>7 and the subtilisin variants are hydrophobic at pH 9.5 a hydrophobic association is made between the secreted enzyme and the 4-MEP on the beads. After incubation the media and cell debris is removed by vacuum filtration while the beads and enzyme are kept on the filter.

To elute the enzyme from the beads the pH is now lowered by washing the filter with an elution buffer (pH 5). Hereby the enzymes part from the beads and can be retrieved from the buffer.

The concentration of the purified subtilisin enzyme variants is assessed by active site titration (AST).

The purified enzyme is incubated with the high affinity inhibitor Cl-2A at different concentrations to inhibit a varying amount of the active sites. The protease and inhibitor binds to each other at a 1:1 ratio and accordingly the enzyme concentration can be directly related to the concentration of inhibitor, at which all protease is inactive. To measure the residual protease activity, a substrate (0.6 mM Suc-Ala-Ala-Pro-Phe-pNA in Tris/HCl buffer) is added after the incubation with inhibitor and during the following 4 minutes the development of the degradation product pNA (paranitrophenol) is measured periodically at 405 nm on an Elisa Reader.

Each of the variants of the invention listed in Table I herein was purified according to the above procedure and subsequently the enzyme concentration was determined.

Known concentrations of the variants of Table I were tested for wash performance in detergents as described below.

Example 3

Wash Performance of Savinase Variants

In order to assess the wash performance of selected subtilase variants in a commercial detergent base composition, washing experiments was performed. The enzyme variants of the present application were tested using the Automatic Mechanical Stress Assay (AMSA). With the AMSA test the wash performance of a large quantity of small volume enzyme-detergent solutions can be examined. The AMSA plate has a number of slots for test solutions and a lid firmly squeezing the textile swatch to be washed against all the slot openings. During the washing time, the plate, test solutions, textile and lid are vigorously shaken to bring the test solution in contact with the textile and apply mechanical stress. For further description see WO 02/42740 especially the paragraph "Special method embodiments" at page 23-24.

Two assays were conducted under the experimental conditions specified below:

| Assay A | |
|---|---|
| Commercial detergent base | Latin American type |
| Detergent dosage | 1.5-2.5 g/l |
| Test solution volume | 160 micro l |
| pH | 10-10.5 adjusted with $NaHCO_3$ |
| Wash time | 14 min. |
| Temperature | 20° C. |
| Water hardness | 6-9° dH |
| Enzyme concentration in test solution | 5 nM, 10 nM and 30 nM |
| Test material | EMPA 117 |

The Latin American type detergent was composed according to the provisions in Detergent Example 1 at page 24 herein. Water hardness was adjusted to 6-9° dH by addition of $CaCl_2$ and $MgCl_2$ ($Ca^{2+}:Mg^{2+}=4:1$) to the test system. After washing the textile pieces were flushed in tap water and air-dried.

| Assay B | |
|---|---|
| Commercial detergent base | European powder type 1 |
| Detergent dosage | 6 g/l |
| Test solution volume | 160 micro l |
| pH | as it is in detergent (app. 10-10.5) |
| Wash time | 20 min. |
| Temperature | 30° C. |
| Water hardness | 6-9° dH |
| Enzyme concentration in test solution | 5 nM, 10 nM and 30 nM |
| Test material | EMPA 116 |

The European powder type detergent was composed according to the provisions in Detergent Example 2 at page 24 herein. Water hardness was adjusted to 15° dH by addition of $CaCl_2*2H_2O$; $MgCl_2*6H_2O$; $NaHCO_3$ ($Ca^{2+}:Mg^{2+}:HCO^{3-}=4:1:10$) to the test system. After washing the textile pieces were flushed in tap water and air-dried.

The performance of the enzyme variant is measured as the brightness of the colour of the textile samples washed with that specific enzyme variant. Brightness can also be expressed as the intensity of the light reflected from the textile sample when ruminated with white light. When the textile is stained the intensity of the reflected light is lower, than that of a clean textile. Therefore the intensity of the reflected light can be used to measure wash performance of an enzyme variant.

Color measurements are made with a professional flatbed scanner (PFU DL2400pro), which is used to capture an image of the washed textile samples. The scans are made with a resolution of 200 dpi and with an output colour dept of 24 bits. In order to get accurate results, the scanner is frequently calibrated with a Kodak reflective IT8 target.

To extract a value for the light intensity from the scanned images, a special designed software application is used (Novozymes Color Vector Analyzer). The program retrieves the 24 bit pixel values from the image and converts them into values for red, green and blue (RGB). The intensity value (Int) is calculated by adding the RGB values together as vectors and then taking the length of the resulting vector:

$$Int = \sqrt{r^2 + g^2 + b^2}.$$

The wash performance (P) of the variants was calculated in accordance with the below formula:

$$P = \text{Int}(v) - \text{Int}(r)$$

where
Int(v) is the light intensity value of textile surface washed with enzyme variant and
Int(r) is the light intensity value of textile surface washed with the reference enzyme subtilisin 309 (BLSAVI).

The results presented in Table IV and V below are Performance Scores (S) summing up the performances (P) of the tested enzyme variants as:

S (2) which indicates that the variant performs better than the reference at all three concentrations (5, 10 and 30 nM) and S (1) which indicates that the variant performs better than the reference at one or two concentrations.

TABLE IV

Wash performance test results, Assay A.

| Mutations | Score | Mutations | Score |
|---|---|---|---|
| G97E + A98S | 2 | V28I + A98AD + T224S | 2 |
| G97D + A98D | 2 | S99AD + M175V + P131F | 1 |
| V95C + G97W + A98E | 2 | S99AD + P131L | 2 |
| V95T + G97A + A98D | 2 | S9R + S99AD + P131W | 1 |
| S103Y + V104M + S106D | 1 | V68A + N116S + V139L + Q245R | 2 |
| V104T + S106D | 2 | S3T + A16P + R45C + G100S + A230V | 2 |
| S3T + A16P + S99SD + S144D + A158T + A230V + T260R | 2 | I8V + S9R + A15T + R19W + V30I + G61D + S99SD + S256N | 2 |
| S103D + V104T + S106T | 1 | V30I + S99SD + S256R | 2 |
| S103D + V104L + S106M | 2 | G61S + S99SD + V244I | 2 |
| S103D + V104T + S106G | 2 | V68A + V139L + S163G + N185S | 2 |
| S103D + V104S + S106A | 2 | S99SD + Y263H | 2 |
| S103H + V104N + S106D | 2 | V104N + S106T | 2 |
| S103E + V104I + S106T | 1 | S99SG + S144D | 1 |
| S103Q + V104T + S106E | 2 | V30I + S99SD | 1 |
| S103E + S106T | 2 | N18H + S99SD | 2 |
| S103E + V104R + S106A | 2 | S9R + T22S + S99SD + K251E | 1 |
| A108T + L111V | 2 | A48T + V68A + P131M | 2 |
| L124I + S125A | 1 | A15M + S99SM + V139I + V244I | 2 |
| L124C + P131* | 2 | P14T + A15M + S99SD | 2 |
| P129S + S130AT | 2 | I8V + S99SD + S144D + A228T | 2 |
| L96LA + A151G + V203A | 1 | I8V + R19K + V139I | 2 |
| S99SD + A108V + V139L | 2 | I35T + N62D | 2 |
| S99SD + S190A | 2 | N62D + S265G | 2 |
| S99SD + V203A | 2 | Q2L + N62D | 2 |
| S99SD + V139I | 1 | N62D + N76D | 2 |
| S99SD + A108V | 2 | R45H + G61E + V68A | 2 |
| S99SD + S106A + A151G | 2 | N62D + V121A | 2 |
| V68A + S106A | 2 | N62D + A215D | 2 |
| V68A + N185D + V203S | 2 | N62D + N238D | 2 |
| V68A + V139L | 2 | N62D + R145G | 2 |
| V68A + V139I | 2 | V4L + N62D + E89G | 2 |
| V68A + A158V | 2 | N62D + S188G + K251R | 2 |
| V68A + V203A | 2 | S49N + N62D | 2 |
| V68A + V203S | 2 | N62NE | 2 |
| V68A + V203L + S259A | 2 | V11A + N62DE | 2 |
| V68A + S106L | 2 | N62ND + N184S + S256G | 2 |
| V30I + V68A + V203S | 2 | N18S + N62D + I107T + A254S | 2 |
| V51A + V68A + S106T + A168G | 1 | S57P + N62ND | 2 |
| V51A + V68A + S106T + A168G | 1 | N62NE + V234I | 2 |
| V68A + N76S + V203M + P239T | 2 | Q137H + R170C + G195E | 1 |
| V68A + V203L | 2 | S99A + S101SA | 2 |
| V68A + L75I + V203Q | 2 | R10K + P14A + R19K + A98AS + S128N | 2 |
| V68A + T71A + V139L | 2 | T22A + R45K + A98AS + S128N | 2 |
| Y192H + V68A | 2 | A98AV + S99D + Y167K | 2 |
| V68A + S106A + A108T | 2 | S9G + P14K + Y167A + R170S | 2 |
| V68A + S106T + A108T | 2 | S9D + P14T + Y167A + R170S | 2 |
| V68S + A108S | 2 | S9R + P14M + A98AD | 1 |
| V68A + N76S + G211D | 2 | S9R + R19L + A98AD + E271A | 2 |
| V68A + S106T + A108T | 1 | S9R + P14S + R19F + A98AD | 2 |
| A151V + R170C | 2 | S99DA + P129PSN + P131A | 2 |
| P14D + A98AS + H120D + G195F + S212N + M222S | 1 | S99AD + V244M + Q245K + N248D + K251R + T255A + S256N | 2 |
| S49N + V203L + N218D | 2 | S9R + P14V + R19G + A98AD | 2 |
| V68A + S106M + N184D | 2 | S99AD + N248P + T255A + S256G | 2 |
| P55S + V68L + A158E + G160A | 2 | *0AQSVPWG + A98AD | 2 |
| V68A + A158C | 2 | T22A + S99AD | 2 |
| V68A + A158L + Y214C | 2 | K94N + A98T + S99L | 2 |
| A88V + S99AD + P131F | 2 | N76D + A174AL + A194P + A230V | 1 |
| P14T + A16P + I72V + S99SD + V244I + T260A | 2 | P40L + N218D + A232S + Q236L + Q245E + S259N | 2 |
| S99AD + P131F | 2 | A232L + Q236L + Q245E | 1 |
| R10H + N62D | 2 | A232T + Q236L + Q245D | 2 |

TABLE IV-continued

Wash performance test results, Assay A.

| Mutations | Score | Mutations | Score |
|---|---|---|---|
| V28I + A98AD + T224S | 2 | R170H + Q236A + Q245R | 2 |
| S9K + T22K + S99AD | 2 | A232L + Q236T + Q245D | 2 |
| P14S + S99AD + P131W | 2 | G97GG + P131H + Q137E + V268L | 2 |
| V68A + I72V + P131F | 2 | A88V + G97GV + P131H | 2 |
| S9R + S99AD | 1 | G97GA + H120Q + S130P + G264E | 2 |
| S9K + S99AD | 2 | G97GG + V139L | 2 |
| V28I + A88V + G100S + P131M | 2 | G97GG + Q137D | 1 |
| S103L + V104S + S106G | 2 | G97GG + H120D + Q137H | 2 |
| V68A + T224A | 2 | N185R | 2 |
| V68A + P131F | 2 | P131H + Q137E | 1 |
| A48T + V68A + P131M | 1 | V104I + H120N + P131H + Q137E | 2 |
| V68A + I72V + P131F | 2 | H120Q + Q137E | 1 |
| G100GE + P131F | 2 | S9R + A15T + G97GV + H120D | 1 |
| S99AD + P131F + T260A | 1 | G100S + H120Q + Q137H | 2 |
| R19G + A98AS | 2 | V68A + H120K + Q137E | 2 |
| G61R + N62D | 1 | G97GA + H120E | 2 |
| V68A + S106M + N184D | 2 | H120D + S128I + Q137D | 2 |
| P55S + V68L + A158E + G160A | 2 | G97GG + P131H | 2 |
| V68A + A158C | 2 | G97GG + H120N + L126I | 2 |
| R19W + G61S + S99SD + N204T + Y263H + S265R | 2 | S9R + A15T + G97GA + H120D + P131H + Q137E | 2 |
| A232C | 2 | S9R + A15T + G97GV + P131T + Q137H | 1 |
| N62D + A232T + Q236C | 2 | S9R + A15T + G20* + L21F + N62D + Q245N | 2 |
| A232P + Q236L + Q245E | 2 | S9L + A15T + T22TV + V139L + Q245F | 2 |
| A232S + Q236L + Q245T + K251E | 2 | S132G + Q245F | 1 |
| S163C + Q236M + Q245T + S256G | 2 | S9R + A15T + T22TG + N62D + V139L + Q245V | 1 |
| N218D + A232L + Q236F + Q245F | 2 | S9L + A15T + T22TV + V139L + Q245F + L262S | 2 |
| S163N + A232L + Q236S + Q245E | 2 | S9R + A15T + T22TL + N62D + Q245W | 2 |
| A232S + Q236S + Q245E | 2 | V68A + A158L + Y214C | 2 |
| V68A + V203L | 2 | N62D + V150I | 2 |
| V68S + A158D | 2 | S3T + P14Q + A15M + R19K + N62D + S144D | 2 |
| I8V + A15T + R19K + A85T + S99SD + A114V + V244I + S256N + Y263H | 2 | P14Q + R19W + V51I + G61E + S99SD + V139I + T260R | 2 |
| L111F + Y263H | 2 | S3T + P14L + H17R + S99SD + V139I + S144D | 2 |
| P52V + S78T + S99SD | 2 | S3A + V30I + S99SD + S106G + N248S | 2 |
| A15M + S99SD + V268I | 2 | I8V + A15T + S99SD | 2 |
| S99G + S128N + N183D + A232L + Q236T + Q245R | 1 | S3T + S9R + P14A + A15M + R19L + S99SD + V139I | 2 |
| S99R + S101SA | 1 | S9R + A15T + G97GG + H120D + Q137E | 2 |
| L96LA + A98T + P131AA | 2 | S9R + A15T + G20A + G97GV + H120D + P131H | 2 |
| A98E + S99P | 2 | S163N + A232L + Q236A + Q245G | 2 |
| V28I + S99AD + P131F | 2 | N173D + A232L + Q236A + Q245N | 2 |
| S9R + A15T + G97GV + Q137H | 1 | P55S + V68A + S106M + A108T + P129T | 2 |
| V81A + P131T + A133S + Q137E | 1 | K27R + V68L + G118D + A158E | 1 |
| N43D + V68A + S106F + N238D | 2 | A98E + S99A + S101SK | 2 |
| V68A + V203F | 2 | V68A + N140D + T143A + S144N | 2 |
| V68A + S106E | 2 | N62D + N140K + T143A + S144D | 2 |
| V68A + S106I | 2 | S9F + P14T + R19L + A98AD | 2 |
| V68A + A158M + R170C | 1 | S9V + P14R + R19F + A98AD | 2 |
| V68A + P129T + N218D | 2 | S99A + S99SD + G258K + L262Q | 2 |
| V68S + P129E | 2 | S87C + S99SA + S99D + P131A | 2 |
| V68S + P129D | 2 | S99A + S99SD + G258K + L262Q | 2 |
| V68L + P129E + N261D | 2 | V28I + S99A + *99aD + P131F | 1 |
| G97GV + H120D | 2 | A85T + G102D + S106T + K237R | 2 |
| P131A + A133ASA | 2 | V68A + T71A | 2 |
| L111F + Y263H | 2 | G61GS | 2 |
| V11A + G61GE + V227A + S240F | 2 | G100L | 2 |
| A133E + S144K + N218D | 2 | A133D | 2 |
| S128A + P129S + S130SP | 2 | V68A | 2 |
| G61GE | 2 | N123D | 2 |

TABLE V

Wash performance test results, Assay B.

| Mutations | Score |
|---|---|
| S9R + A15T + T22TW + N204D + Q245I | 2 |
| S9R + A15T + G97GG + P131S + Q137H | 2 |
| S9R + A15T + T22TG + N62D + V139L + Q245G | 2 |
| S9R + A15T + T22TL + N62D + I107V + V139L + Q245W | 2 |
| S9G + A15T + G97GA + Q137H | 1 |
| S9R + A15T + V68A + Q245R | 2 |
| S9R + A15T + G97GA + H120N + S212L | 2 |

TABLE V-continued

Wash performance test results, Assay B.

| Mutations | Score |
|---|---|
| S9R + A15T + L96LG + H120D + P131H + R186L | 2 |
| S9R + A15T + G97GA + H120D + Q137D | 2 |
| S9R + A15T + A16P + G97GA + P131S + Q137D + N204S | 2 |
| S9R + A15T + L21LP + T22TV + M119I + N218D + Q245I | 2 |
| S9R + A15T + G97GV + H120D + Q137H | 1 |
| S9R + A15T + L96LG + H120N + P131H + Q137E | 2 |
| S9R + A15T + L96LG + H120D + P131S + Q137E | 2 |
| S9R + A15T + H120N + P131T + N218D | 2 |
| V4A + S9R + A15T + G97GV + H120D | 1 |
| S9R + A15T + L96LG + H120D + G160D | 2 |
| S9R + A15T + T22TG + N62D + V139L + Q245S | 2 |
| S9R + A15T + G61E + A85T + P239L + Q245C | 2 |
| S9R + A15T + P131H + S144P | 2 |
| S9R + A15T + G97GA + Q137E | 2 |
| S9R + A15T + G97GA + H120Q + P131H + Q137E | 2 |
| S9R + A15T + L21LW + G100S + V139L + Q245V | 1 |
| S9R + A15T + G97GA + Q137H + N218S | 2 |
| S9R + A15T + L96LG + H120N + P131S + Q137H | 2 |
| S9R + A15T + G97GA + H120N + Q137E | 2 |
| S9R + A15T + L96LG + P131T + Q137H | 2 |
| S9R + A15T + L96LG + H120N + P131S | 2 |
| S9R + A15T + V68A + Q137D | 1 |
| S9R + A15T + G97GA + H120Y + Q137H | 2 |
| S9R + A15T + G97GA + Q137D | 2 |
| S9R + A15T + K94N + H120N + P131H | 1 |
| S9R + A15T + L96LG + P131H + Q137D | 2 |
| S9R + A15T + F50S + H120D + P131H | 2 |
| S9R + A15T + G97GA + H120N + Q137D + N248D | 2 |
| S9R + A15T + L96LG + P131Q + Q137D | 2 |
| S9R + A15T + T22G + V139L + Q245L | 2 |
| V139L + Q245R | 2 |
| S9R + A15T + Q245F | 2 |
| S9R + A15T + Q245S | 2 |
| S9R + A15T + G97GV + H120Q | 1 |
| S9R + A15T + G97GA + Q137E + L262V | 1 |
| S9R + A15T + G127E + P131R + Q137H | 2 |
| S9R + A13V + A15T + I35V + N62D + Q245F | 2 |
| S9R + A15T + Q245V | 2 |
| V139L + Q245F | 2 |
| S9R + A15T + T22A + V139L + Q245E | 2 |
| S9R + A15T + T22L + V139L + Q245V + A254S | 2 |
| S9R + R19L + A98AD | 2 |
| P14R + A98AD | 2 |
| S9R + A15T + Q245L | 2 |
| S9R + A15T + G61E + A85T + P239S + Q245V | 2 |
| S9R + A15T + G61E + A85T + Q206L + Q245R | 2 |
| P239T + Q245R | 2 |
| S9R + A15T + N62NG + Q245T | 2 |
| S9R + A15T + G61GP + Q245L | 2 |
| S9R + A15T + G61E + A85T + Q137H + Y209C + Q245G | 2 |
| S9R + A15T + G61E + A85T + P239S + Q245C | 2 |
| V68I + A98AD | 2 |
| V68A + N269K | 1 |
| N62D + Q245A + N252G + S265G | 2 |
| N218D + Q245G + N252H | 2 |
| S9R + A15T + G102S + M175T + Q245R + N252D | 2 |
| S9R + A15T + N62D + Q245W + N252V | 2 |
| S9R + A15T + N62D + Q245R + N252M | 2 |
| S9R + A15T + N62D + Q245W + N252S | 2 |
| S99SD + N204S + Q245R | 1 |
| N62D + Q245R | 2 |
| N62D + A151G | 1 |
| V68A + S106T | 2 |
| S99A + S99SD + V203L | 2 |
| A98AD + A215T | 2 |
| N62D + Q245G + N252T | 2 |
| A152P + Q245R + N252T | 2 |
| S163N + T213A + Q245R | 2 |
| S106L + Q245R + N252E | 2 |
| Q245W + N252Y | 2 |
| Q245W + N252V | 2 |
| R45H + Y171C + Q245W + N252S | 2 |
| G20R + A48T + R170C + Q245W + N252Q | 2 |
| N62D + N252T | 2 |
| N218D + Q245W + N252E | 2 |

TABLE V-continued

Wash performance test results, Assay B.

| Mutations | Score |
|---|---|
| G20R + R170C + Q245R + N252V | 2 |
| S9R + P14I + R19K + A98AD + T274S | 2 |
| A98AE + V203I | 2 |
| V51A + V68A + S163G + V203A | 2 |
| N62D + Q245W + N252H | 2 |
| N62D + Q245W + N252A | 2 |
| G20R + N62D + V244I + Q245W + N252E | 2 |
| N204D + Q245S | 2 |
| N62D + Q245W + N252E | 2 |
| N62D + Q245R + N252V | 2 |
| S9R + A15T + S24P + G61E + A85T + P239S + Q245A | 2 |
| G102S + M222S + Q245L + N252D | 2 |
| A15M + V30I + N62D + S99N + L111I + V244A + S265N | 2 |
| V68A + S106A + G118D + Q245R + T255S + L257G + T274L | 2 |
| S3T + Q12D + R19W + V30I + S106G + I107M | 2 |
| V68A + A88T + V139L | 2 |
| V51I + L111I + G118D + Q245R | 2 |
| V68A + V203L | 1 |
| A1T + V68A + N116D + G118D | 1 |
| V68A + G118D + Q245R | 2 |
| N62D + V139I + N183D + N185S + V203I + Q245R + L262S | 2 |
| N62D + I72V | 1 |
| N62D + V81A + Q245R | 1 |
| T22A + V68A + S106T + G118D | 1 |
| V68A + L111I + V203I | 1 |
| G61E + V68A + A169G | 1 |
| V68A + L111V | 1 |
| V68A + G118D + V203A + K251R | 1 |
| V68A + G118D | 1 |
| A1V + V51A + V68A + V203I | 2 |
| V68A + V139L + A223G | 1 |
| N62D + Y214H + K237R | 1 |
| V68A + S106A + G118D + Q245R | 2 |
| S9R + A15T + T22A + N62D | 2 |
| A98Q + S99D | 1 |
| S9R + P14I + R19K + A98AD | 2 |
| S9R + A15M + A16P + T22S + S99AD | 1 |
| S99AD + T255R + S256N | 2 |
| S9R + A15T + T22TQ + S101P | 1 |
| S9R + A15T + H120R + Q137D + N173S | 2 |
| G97E | 1 |
| Q245W | 2 |
| S9R + A15T + L96LG + Q137E + Y209H | 2 |
| S9R + A15T + L111V + Q137E + G211D | 1 |
| S9R + A15T + L111I + Q137E | 2 |
| S9R + A15T + L111I + H120N + Q137E | 2 |
| S9R + A15T + L96LG + H120Q + Q137E | 1 |
| S9R + A15T + T260M | 2 |
| S9R + A15T | 2 |
| Q245I | 2 |
| S9R + A15T + H120G + Q137E + N218D | 2 |
| S9R + A15T + S130P | 2 |
| Q245F | 2 |
| S9R + A15T + N218D | 2 |
| G63E + N76D + A194P + A230V | 2 |
| S9R + A15T + T224A | 2 |
| G100S | 2 |
| S9R + A15T + D60DG | 1 |
| A138V + V139I + A194P + N218D + A230V | 2 |
| A108V + A169G + R170A + Y171H | 1 |
| I8V + P14L + R19L + V30I + I35V + S57P + P129S + Q137D + S144D + S256N | 2 |
| A133D + T134S + Q137A | 1 |
| Q137D | 2 |
| A98AH | 1 |
| V51D | 2 |
| Q12E + P14L + A15T | 2 |
| G63E + N76D + A194P + A230V | 2 |
| Q12E + P14L + A15T | 2 |
| G97GS | 1 |
| M222S + Q245G + N252G | 1 |
| V68I + V203L | 2 |
| V51A + S163T | 2 |
| S106A + A138G | 2 |
| V139I + A151G | 2 |
| S9R + A15T + S99C + H120N + P131S + Q137H + M222S | 2 |

TABLE V-continued

Wash performance test results, Assay B.

| Mutations | Score |
|---|---|
| S9R + A15T + S99G + G100S + H120N + P131S + Q137H | 2 |
| A15T + N185D + M222S + Q245R + N252V | 2 |
| S9R + A15T + T22TL + G61E + L96LG + Q137D + Q245R | 2 |
| S9R + T22TL + G61E + G97GG + M119I + P131T | 2 |
| Y209H + M222S + Q245G + N252L | 2 |
| M222S + Q245M + N252E | 2 |
| S9R + A15T + N62D + H120N + P131T | 2 |
| S9R + A15T + V68A + N218D + Q245R | 2 |
| S9R + A15T + V68A + H120N + N218D + Q245R | 1 |
| S9R + A15T + V68A + A174V + Q245R | 2 |
| S9R + A15T + G46D + V68A + N218D + Q245R | 2 |
| G97D + A98N + S128G + S130T + P131D + T134A | 2 |
| S9R + A15T + V68A + A98M + Q245R + N248D | 2 |
| S9R + A15T + V68A + A98L + S99G + Q245R | 2 |
| S9R + A15T + A98G + S99C + H120N + P131S + Q137H | 2 |
| S9R + A15T + T38S + A98R + S99C + G100S + H120N + P131S + Q137H | 2 |
| A98V + S99C + Q245R | 1 |
| S9R + A15T + A98S + G100S + H120N + P131S + Q137H | 1 |
| S9R + A15T + G20* + L21F + N62D + Q245R | 2 |
| S9R + A15T + G20* + L21F + N62D + Q245R + S259G | 2 |
| A98S + G100S + Q245R | 2 |
| A98L + S99C + Q245R | 2 |
| S9R + A15T + G20* + L21F + N62E + Q245R | 2 |
| S9R + A15T + G20* + L21F + P52T + N62D + Q245R | 2 |
| S9R + A15T + V68A + S99G + Q245R + N261D | 2 |
| N62D + P131F + A172V | 2 |
| N62D + P131F | 2 |
| S99SD + Q245R | 2 |
| S9R + A13T + S99A + S99SD + P131F | 2 |
| S9R + A15T + N62S + H120N + P131T + N218D | 2 |
| A98R + G100C + Q245R | 2 |
| A98G + S99C + Q245R | 2 |
| A98T + S99G + G100S + S240F + Q245R | 2 |
| S9R + A15T + H120N + P131T + N218D + N269T | 2 |
| S9R + A15T + G61E + H120S + Q137D + V139L + N218D | 2 |
| S9R + A15T + L96LG + H120N + P131S + Q137H + M222S | 1 |
| S9R + A15T + G61E + A98S + S99M + Q245R | 2 |
| A98G + G100S + Q245R + N261D | 2 |
| S9R + A15T + V68A + A98L + Q245R | 1 |
| S9R + A15T + V68A + A98G + S99V + Q245R | 1 |
| S9R + A15T + V68A + A98M + S99G + Q245R + T274A | 2 |
| S9R + A15T + G61E + V68A + A98S + S99G + Q245R | 2 |
| S9R + A15T + A88V + A98R + S99G + G100C + H120N + P131S + Q137H | 1 |
| S9R + A15T + A98C + G100S + H120N + P131S + Q137H | 1 |
| S9R + A15T + G20* + L21F + G61E + *61aP + Q245R | 1 |
| S9R + A15T + V68A + A98G + S99I + K237R + Q245R | |
| S9R + A15T + V68A + H120N + P131S + Q137H + Q245R | 2 |
| A98S + S99G + G100S + Q245R | 2 |
| S9R + A15T + V68A + H120D + P131S + Q137H + Q245R | 2 |
| A98T + S99G + G100S + Q245R | 2 |
| S9R + A15T + A98S + S99G + G100S + H120N + P131S + Q137H | 2 |
| V68A + S106A + Q245R + N252D | 2 |
| V68A + S106A + Q245W | 2 |
| V68A + S106A + N252M + Y263C | 1 |
| V68A + S106A + Q245W + N252K | 0 |
| V68A + S106A + A174V + Q245R + N252D | 1 |
| S9R + A15T + V68A + Q245R + N252S | 2 |
| S9R + A15T + V68A | 2 |
| S9R + A15T + G20* + L21F + *61aS + V68A + G160D + Q245R | 2 |
| S9R + A15T + Y167I + R170L | 2 |
| S9R + A15T + G20* + L21F + *63aG + Q245R + N272V | 2 |
| S9R + A15T + G20* + L21F + *61aA + V68A + Q245R | 2 |
| S9R + A15T + V68A + A194T + Q245R + N252E | 2 |
| S9R + A15T + G20* + L21F + *62aS + N218D + Q245R | 2 |
| V68A + S106A + T213A | 2 |
| S9R + A15T + V28I + V68A + Q245R + N252A | 2 |
| V68A + S105G + S106A | 2 |
| S9R + A15T + V68A + H120N + P131S + Q137H + Q245M | 2 |

| Assay C | |
|---|---|
| Commercial detergent base | European powder type 2 |
| Detergent dosage | 4 g/l |
| Test solution volume | 160 micro l |
| pH | as it is in detergent (app. 10-10.5) |
| Wash time | 20 min. |
| Temperature | 30° C. |
| Water hardness | 6-9° dH |
| Enzyme concentration in test solution | 5 nM, 10 nM and 30 nM |
| Test material | EMPA 116 |

The European powder type detergent was composed according to the provisions in Detergent Example 2. Water hardness was adjusted to 15° dH by addition of $CaCl_2*2H_2O$; $MgCl_2*6H_2O$; $NaHCO_3$ ($Ca^{2+}:Mg^{2+}:HCO^{3-}=4:1:10$) to the test system. After washing the textile pieces were flushed in tap water and air-dried.

TABLE VI

Wash performance test results, Assay C.

| Mutations | Score |
|---|---|
| Q12E + P14L + A15T | 2 |
| P14R + A98AD | 2 |
| G100S | 2 |
| A169G + R170H | 1 |
| A98AD + A169G | 1 |
| A138V + V139I + A194P + N218D + A230V | 2 |
| S99A + S99SD + V203L | 1 |
| V68A + S106T | 1 |
| A98AD + A215T | 2 |
| A108V + A169G + R170A + Y171H | 1 |
| S3L + N62D + S163A + S190A | 2 |
| S9R + P14I + R19K + A98AD + T274S | 2 |
| S9R + A15T + G61E + A85T + N218D + P239S + Q245L | 2 |
| S9R + A15T + S24P + G61E + A85T + P239S + Q245A | 2 |
| S99SD + P131F | 1 |
| N62D + P131F + A172V | 1 |
| N62D + P131F | 1 |
| V68A + A88T + V139L | 2 |
| V68A + G118D + V203A | 2 |
| P40L + V68A + A108T + A138V + V203I | 2 |
| I8T + A98AD + T274R | 2 |
| A98AE + V203I | 2 |
| V51A + V68A + S163G + V203A | 2 |
| A1V + V51A + V68A + V203I | 2 |
| V68A + G100S | 1 |
| V68A + V203L | 2 |
| A1T + V68A + N116D + G118D | 1 |
| N62D + A169G + V203I + Q245R | 1 |
| G23S + S99SD + A194P + S242T + Q245R + T274R | 1 |
| S99SD + N204S + Q245R | 2 |
| N62D + Q245R | 2 |
| V68A + S106A + G118D + Q245R | 2 |
| V51I + L111I + G118D + Q245R | 2 |
| N62D + V139I + N183D + N185S + V203I + Q245R + L262S | 2 |
| N62D + I72V | 1 |
| S9R + R19L + A98AD | 2 |
| S9G + P14R + R19I + A98AD | 1 |
| S9R + A15T + T22L + V139L + Q245V + A254S | 2 |
| S9R + A15T + T224A | 2 |
| S9R + A15T + Q245L | 2 |
| S9R + A15T + N62NG + Q245T | 1 |
| S9R + A15T + N62ND + V139L + Q245E | 2 |
| S9R + A15T + N62ND + V139L + N261D | 2 |
| Y167I + R170L + Q245E | 1 |
| Y167I + R170L + Q245R | 2 |
| Y167I + R170L + Q245M | 1 |
| Y167I + R170L | 2 |
| S99SE + Q245R | 2 |
| S9R + A15T + G61E + A85T + Q137H + Y209C + Q245G | 2 |
| S9R + A15T + G61E + A85T + P239S + Q245C | 1 |

TABLE VI-continued

Wash performance test results, Assay C.

| Mutations | Score |
|---|---|
| G102S + M222S + Q245L + N252D | 1 |
| N62D + Q245A + N252G + S265G | 1 |
| N62D + Q245G + N252T | 1 |
| S9R + A15T + N62D + Q245W + N252V | 2 |
| S9R + A15T + N62D + Q245R + N252M | 2 |
| S9R + A15T + N62D + Q245W + N252S | 1 |
| S163N + T213A + Q245R | 2 |
| S106L + Q245R + N252E | 2 |
| Q245W + N252Y | 2 |
| Q245W + N252V | 1 |
| G20R + A48T + R170C + Q245W + N252Q | 2 |
| N62D + N252T | 2 |
| N218D + Q245W + N252E | 2 |
| G20R + R170C + Q245R + N252V | 2 |
| N62D + Q245W + N252H | 2 |
| N62D + Q245W + N252A | 2 |
| G20R + N62D + V244I + Q245W + N252E | 2 |
| N204D + Q245S | 1 |
| N62D + Q245W + N252E | 2 |
| N62D + Q245R + N252V | 2 |
| A98L + S99C + Q245R | 2 |
| N62D + A98R + Q245R | 2 |
| S9R + A15T + V68A + S99G + Q245R + N261D | 2 |
| S9R + A15T + G20* + L21F + N62D + Q245R | 2 |
| S9R + A15T + G20* + L21F + N62E + Q245R | 2 |
| V68I + A98AD | 2 |

| Assay D | |
|---|---|
| Commercial detergent base | European powder type 1 |
| Detergent dosage | 6 g/l |
| Test solution volume | 160 micro l |
| Ph | as it is in detergent (app. 10-10.5) |
| Wash time | 20 min. |
| Temperature | 30° C. |
| Water hardness | 6-9° dH |
| Enzyme concentration in test solution | 5 nM, 10 nM and 30 nM |
| Test material | C-10 swatches from Center for Testmaterials, Vlaardingen, NL |

The European powder type detergent was composed according to the provisions in Detergent Example 2 at page 24 herein. Water hardness was adjusted to 15° dH by addition of $CaCl_2*2H_2O$; $MgCl_2*6H_2O$; $NaHCO_3$ ($Ca^{2+}:Mg^{2+}:HCO^{3-}=4:1:10$) to the test system. After washing the textile pieces were flushed in tap water and air-dried.

TABLE VII

Wash performance test results, Assay D.

| Mutations | Score |
|---|---|
| G97GS | 1 |
| S9V + P14R + R19F + A98AD | 1 |
| S9R + A15T + L111I + Q137E | 1 |
| S9R + A15T + G97GA + Q137E | 2 |
| S9R + A15T + L96LG + Q137E + Y209H | 1 |
| S9R + A15T + L96LG + H120N + P131S | 2 |
| S9R + A15T + G97GV + H120Q | 2 |
| S9R + A15T + L96LG + H120Q + Q137E | 2 |
| S9R + A15T + G97GV + P131S | 2 |
| S9R + A15T + K94N + H120N + P131H | 1 |
| S9R + A15T + N76S + L111V + P131H + Q137D | 1 |
| S9R + A15T + F50S + H120D + P131H | 2 |
| S9R + A15T + L96LG + S130* | 2 |
| S9R + A15T + L96LG + P131Q + Q137D | 2 |

TABLE VII-continued

Wash performance test results, Assay D.

| Mutations | Score |
|---|---|
| S9R + A15T + G97GA + H120D + Q137H + M222V | 1 |
| S9R + A15T + G97GA + H120N + Q137D + N248D | 2 |
| S9R + A15T + L21LW + G100S + V139L + Q245V | 1 |
| S9R + A15T + G20* + L21F + N62D + Q245N | 2 |
| S9R + A15T + L21LC + V139L + R186H + Q245M | 1 |
| S132G + Q245F | 1 |
| S9R + A15T + T22TG + N62D + V139L + Q245G | 2 |
| S9R + A15T + T22TL + N62D + I107V + V139L + Q245W | 2 |
| S9R + A15T + T22TQ + S101P | 2 |
| S9R + A15T + T22TG + N62D + V139L + Q245V | 1 |
| S9R + A15T + T22TL + N62D + Q245W | 2 |
| S9R + A15T + T22TW + N204D + Q245I | 2 |
| S9R + A15T + T22TG + N62D + V139L + Q245S | 2 |
| S9R + A15T + L21LP + T22TY + V139L + G160D + Q245L | 1 |
| Q245W | 2 |
| S9R + A15T + S130P | 2 |
| S9R + A15T + G61E + A85T + P239L + Q245C | 2 |
| S9R + A15T + L21LP + T22TV + M119I + N218D + Q245I | 2 |
| S9R + A15T + V68A + Q245R | 2 |
| S9R + A15T + T22A + V139L + Q245E | 2 |
| V139L + Q245R | 2 |
| S9R + A15T + Q245F | 2 |
| S9R + A15T + Q245S | 2 |
| S9R + A15T + T260M | 2 |
| S9R + A15T | 2 |
| S9R + A15T + L21LG + T22TV + V139L + N204D + Q245N | 1 |
| V139L + Q245F | 2 |
| S9R + A15T + T22G + V139L + Q245L | 2 |
| S9R + A15T + Q245V | 1 |
| Q245F | 2 |
| S9R + Q245C | 2 |
| S9R + A15T + N218D | 1 |
| S9R + A13V + A15T + I35V + N62D + Q245F | 2 |
| S99G + S128N + N183D + A232L + Q236T + Q245R | 2 |
| S163N + A232L + Q236A + Q245G | 2 |
| S163C + Q236M + Q245T + S256G | 1 |
| N218D + A232L + Q236F + Q245F | 1 |
| S163N + A232L + Q236S + Q245E | 2 |
| G97GA + H120E | 1 |
| G97GG + P131H | 2 |
| S9R + A15T + G97GA + H120D + P131H + Q137E | 1 |
| S9R + A15T + G97GV + Q137H | 2 |
| S9R + A15T + G97GV + H120N | 2 |
| S9R + A15T + G97GG + P131S + Q137H | 2 |
| S9R + A15T + G97GG + H120N + Q137D | 2 |
| S9R + A15T + H120Q + P131C + Q137H | 2 |
| S9R + A15T + G97GV + H120D + Q137H | 2 |
| S9R + A15T + A16P + G97GA + P131S + Q137D + N204S | 2 |
| S9R + A15T + G97GG + H120D + P131H + Q137H | 1 |
| S9R + A15T + G97GV + H120E + Q137H | 2 |
| S9R + A15T + G97GV + P131T + Q137H | 1 |
| S9R + A15T + G97GV + H120Q + Y263F | 2 |
| S9R + A15T + G97GV + S106A + P131H | 1 |
| S9R + A15T + G97GG + L111I + P131T + Q137H | 1 |
| S9R + A15T + G97GV + P131H + Q137H | 2 |
| S9R + A15T + G20A + G97GV + H120D + P131H | 1 |
| S9R + A15T + G97GA + H120D + P131S + Q137E | 1 |
| S9G + A15T + G97GA + Q137H | 1 |
| S9R + A15T + H120R + Q137D + N173S | 1 |
| S9R + A15T + L96LG + H120N + P131H + Q137E | 2 |
| S9R + A15T + L96LG + H120D + P131S + Q137E | 2 |
| S9R + A15T + H120N + P131T + N218D | 2 |
| S9R + A15T + G97GA + H120D + Q137D | 2 |
| S9R + A15T + L96LG + H120D + P131H + R186L | 2 |
| S9R + A15T + G97GA + R186C | 2 |
| V4A + S9R + A15T + G97GV + H120D | 1 |
| S9R + A15T + L96LG + H120D + G160D | 2 |
| S9R + A15T + G97GA + H120N + S212L | 2 |
| S9R + A15T + G97GA + Q137H + N218S | 2 |
| S9R + A15T + H120D + Q137D | 2 |
| S9R + A15T + N77S + L96LG + H120D + P131Q | 1 |
| S9R + A15T + G97GA + H120N + Q137E | 1 |
| S9R + A15T + G97GA + Q137E + L262V | 2 |
| S9R + A15T + P131H + S144P | 2 |
| S9R + A15T + G127E + P131R + Q137H | 2 |

The invention claimed is:

1. An isolated variant of a parent subtilase comprising a set of amino acid substitutions corresponding to residues selected from the group consisting of:
S9R+A13V+A15T+I35V+N62D+Q245F; and
S9R+A15T+G20*+L21F+N62D+Q245N;
wherein each amino acid position is numbered by correspondence to a position in the amino acid sequence of subtilisin BPN' as set forth in SEQ ID NO:1.

2. An isolated variant of a parent subtilase comprising a set of amino acid substitutions corresponding to residues selected from the group consisting of:
S9R+A15T+T22TG+N62D+V139L+Q245G;
S9R+A15T+T22TG+N62D+V139L+Q245S;
S9R+A15T+T22TG+N62D+V139L+Q245V;
S9R+A15T+T22TL+N62D+I107V+V139L+Q245W; and
S9R+A15T+T22TL+N62D+Q245W;
wherein each amino acid position is numbered by correspondence to a position in the amino acid sequence of subtilisin BPN' as set forth in SEQ ID NO:1.

3. The isolated subtilase variant of claim 1 or claim 2, wherein the parent subtilase belongs to sub-group I-S1.

4. The isolated subtilase variant of claim 1 or claim 2, wherein the parent subtilase belongs to sub-group I-S2.

5. The isolated subtilase variant of claim 1 or claim 2, wherein the parent subtilase is subtilisin 309.

6. A cleaning or detergent composition, comprising the isolated subtilase variant of claim 1 or claim 2 and a surfactant.

7. The composition of claim 6, which comprises one or more additional enzymes.

8. The composition of claim 7, which additionally comprises one or more enzymes selected from the group consisting of an amylase, a cellulase, a cutinase, an esterase, a beta-galactosidase, a glycoamylase, a hemicellulase, a lactase, a ligninase, a lipase, a polygalacturonase, and a protease.

9. An isolated DNA sequence encoding the subtilase variant of claim 1 or claim 2.

10. An expression vector comprising the isolated DNA sequence of claim 9.

11. A microbial host cell transformed with the expression vector of claim 10.

12. The microbial host cell of claim 11, which is a *Bacillus* host cell.

13. A method for producing a subtilase variant, comprising
(a) culturing the host of claim 11 under conditions conducive to the expression and secretion of the subtilase variant, and
(b) recovering the secreted subtilase variant from the culture.

* * * * *